US008184279B2

(12) United States Patent
Feldkhun

(10) Patent No.: US 8,184,279 B2
(45) Date of Patent: May 22, 2012

(54) FOURIER DOMAIN SENSING

(75) Inventor: Daniel Feldkhun, Boulder, CO (US)

(73) Assignee: The Regents of the University of Colorado, a Body Corporate, Denver, CO (US)

(*) Notice: Subject to any disclaimer, the term of this patent is extended or adjusted under 35 U.S.C. 154(b) by 382 days.

(21) Appl. No.: 12/485,858

(22) Filed: Jun. 16, 2009

(65) Prior Publication Data

US 2009/0316141 A1 Dec. 24, 2009

Related U.S. Application Data

(60) Provisional application No. 61/061,745, filed on Jun. 16, 2008.

(51) Int. Cl.
G01J 1/36 (2006.01)
(52) U.S. Cl. ....................... 356/217; 250/351
(58) Field of Classification Search ............. 356/217; 250/351; 382/206, 232, 254
See application file for complete search history.

(56) References Cited

U.S. PATENT DOCUMENTS

| 4,541,697 | A | * | 9/1985 | Remijan .................. 351/211 |
| 4,584,484 | A | | 4/1986 | Hutchin |
| 5,384,573 | A | | 1/1995 | Turpin |
| 5,394,268 | A | | 2/1995 | Lanni et al. |
| 5,751,243 | A | | 5/1998 | Turpin |
| 6,016,196 | A | | 1/2000 | Mermelstein |
| 6,055,097 | A | | 4/2000 | Lanni et al. |
| 6,255,642 | B1 | | 7/2001 | Cragg et al. |
| 7,339,170 | B2 | * | 3/2008 | Deliwala .................. 250/351 |
| 2006/0061770 | A1 | * | 3/2006 | Erskine .................. 356/484 |

OTHER PUBLICATIONS

Ustinov, N.D. et al., "Active Aperture Synthesis in Observation of Objects Via Distorting Media," Sov. J. Quantum Electron., vol. 17, No. 1, pp. 108-110, Jan. 1987.
U.S. Appl. No. 13/247,610, filed Sep. 28, 2011, Feldkhun.
Ben-Yosef, N. et al., "Real-Time Spatial Filtering Utilizing the Piezo-electric-Elasto-Optic Effect," Optica Acta, vol. 29, No. 4, pp. 419-423, 1982.
Korpel, Adrianus et al., "The Interchange of Time and Frequency in Television Displays," Proceedings of the IEEE, vol. 57, No. 2, pp. 160-170, Feb. 1969.

* cited by examiner

Primary Examiner — Layla Lauchman
(74) Attorney, Agent, or Firm — Perkins Coie LLP

(57) ABSTRACT

Methods, systems, and apparatuses are provided for measuring one or more sinusoidal Fourier components of an object. A structured second radiation is generated by spatially modulating a first radiation. The structured second radiation illuminates the object, The structured second radiation is scaled and oriented relative to the object. The object produces a third radiation in response to the illuminating. A single-element detector detects a portion of the third radiation from multiple locations on the object substantially simultaneously for each spatial modulation of the first radiation and for each orientation of the second radiation. A time-varying signal is produced based on said detected portion of the third radiations. One or more characteristics of the one or more sinusoidal Fourier components of the object are estimated based on the time-varying signal.

29 Claims, 11 Drawing Sheets

FOURIER DOMAIN SENSING

CROSS-REFERENCES TO RELATED APPLICATIONS

This application is a non-provisional of, and claims the benefit of, U.S. Provisional Patent Application Ser. No. 61/061,745, entitled "FOURIER ANALYSIS AND SYNTHESIS TOMOGRAPHY," filed Jun. 16, 2008, the entire disclosure of which is incorporated herein by reference for all purposes.

BACKGROUND

The present invention relates to the fields of image sensing and microscopy, and more specifically to methods, systems, and apparatuses for measuring the spatial frequency spectrum of an object using dynamic interference patterns.

Wide-field lens-based imaging systems form images by causing light diffracted or emitted by the object to interfere on a resolving detector or multi-element detector array. From the perspective of Fourier optics, the object may be considered as a coherent sum of sinusoidal Fourier components, such that the angle of light diffracted or emitted by each Fourier component varies with may be proportional to its spatial frequency. Because the optical system can collect only a cone of light defined by its numerical aperture (NA), off-axis light that carries high spatial frequency information may be rejected, thereby limiting spatial resolution. Wavefront aberrations in the optical path may further reduce resolution. Moreover, because the depth of field (DOF) of lens-based imaging systems typically has an inverse quadratic dependence on the NA, high-resolution imaging systems can maintain focus within a very limited depth range, typically only a few wavelengths. Furthermore, due to the challenges of manufacturing large, high NA, high-precision optics, the objective lens is typically be located within a working distance (WD) of only a few millimeters from the object in high-resolution microscopes.

Super-resolution wide-field microscopy techniques in the literature often exploit structured illumination in conjunction with a lens-based imaging system in order to surpass the diffraction resolution limit. Such techniques typically process a sequence of images acquired as the object is illuminated with multiple patterns, such as phase-shifted sinusoids, thereby effectively down-converting high-frequency Fourier components to lower spatial frequencies via the Moire effect. This approach is generally be subject to the same NA-dependent limit on DOF and WD as conventional imaging systems and trades imaging speed for gain in resolution.

Extending the lateral resolution limit even further, U.S. Pat. No. 6,255,642, incorporated herein by reference, may describe the use of an evanescent field produced by standing wave illumination due to total internal reflection at an interface with a transparent optical material in order to perform super-resolution imaging in the near-field. U.S. Pat. Nos. 5,394,268 and 6,055,097, incorporated herein by reference, may describe related structured illumination imaging techniques wherein the object is illuminated with interference patterns directed along the optical axis to reduce the effective DOF of the system, which may enable sub-wavelength axial sectioning.

On the other hand, lensless projection and diffraction tomography techniques may be used for high-resolution imaging of two-dimensional and three-dimensional structures by directly measuring the angular distribution of radiation transmitted or diffracted by an object, and are often used in wavelength regimes, such as X-rays, where lens-based optical imaging is challenging. These techniques typically rely on multiple radiation sources and detectors to measure Fourier components of the object along distinct paths in Fourier space, and a number of methods have been developed for reconstructing two- and three-dimensional images from such tomographic measurements, including the widely-used Filtered Backprojection algorithm.

A structured illumination remote sensing approach, called Fourier Telescopy, has been proposed (see Ustinov, N. D. et al., Sov. J. Quantum Electron. 17, 108-110 (1987), incorporated herein by reference) wherein the object is illuminated with one or more sinusoidal interference patterns that may be generated by an array of radiation sources and the response from the object is recorded with a single-element non-resolving detector to measure one or more Fourier components of a remote object.

U.S. Pat. No. 4,584,484, incorporated herein by reference, may describe a technique wherein an object is illuminated with a moving interference pattern produced by a pair of laser beams. In this technique, light transmitted by the object in response to the illumination is recorded as the angular separation or wavelength of the illuminating beams is mechanically scanned using an arrangement of mirrors during the motion of the pattern, thereby measuring the object's complex spatial Fourier transform along a direction. Additional "Fourier slices" may be acquired by rotating the illumination with respect to the object. An image may be synthesized by Fourier-transforming the acquired data.

U.S. Pat. Nos. 5,384,573 and 5,751,243, incorporated herein by reference, may describe an optical imager similar in principle to Synthetic Aperture Radar, where coherently scattered radiation from the object is detected as the optical plane orientation and the angular separation between an illumination beam and the line of sight of a single-element detector are varied. An optical heterodyne Fourier processor may be used to sequentially synthesize the image.

U.S. Pat. No. 6,016,196, incorporated herein by reference, may describe an optical sensing system that may rely on modulated interference patterns produced by multiple pairs of discrete beams of radiation to measure multiple Fourier components of the object at once without moving components. This technique may be used to characterize or form images of fluorescent, transmissive, and scattering objects.

There is thus a need for tools and techniques that may not be limited to sequential sampling of Fourier components along a direction. Furthermore, there is a need for tools and techniques that may not rely on interference of discrete beams of radiation. Moreover, there is a need for tools and techniques that may provide a flexible, programmable means for measuring a variety of distributions of Fourier components in two and three-dimensional Fourier space through real-time electronic control. In addition, there is a need for tools and techniques that may provide for high speed one, two, and/or three dimensional image acquisition and synthesis.

BRIEF SUMMARY

Certain embodiments thus provide tools and techniques for high-speed Fourier-domain sensing that may address these needs. Embodiments may provide flexible methods, systems, and apparatuses for measuring multiple Fourier components of an object. This may be accomplished in some embodiments by spatially-modulating a radiation wavefront using a combination of dynamic sinusoidal patterns, projecting the modulated radiation onto the object, and detecting the scattered, reflected, transmitted, fluoresced, or otherwise generated response with one or more single-element detectors.

Certain embodiments may not be limited to sequential sampling of Fourier components along a direction and may not rely on interference of discrete beams of radiation. Furthermore, certain embodiments may include methods, systems, and/or apparatuses for tomographic real-time two- and three-dimensional image synthesis using electronic and optical means, high-speed wavefront spatial modulation and rotation, parallel Fourier-domain sampling using RF frequency and optical wavelength multiplexed illumination, optical and electronic heterodyne detection, and/or dynamic optical transfer function control. By applying these techniques, it may not only be possible to engineer a focus-free high-resolution microscope that does not rely on precision optics for high-speed imaging of biological and synthetic structures, but also to implement super-resolution imaging, light-efficient Fourier-domain filtering, wavefront correction, object classification, compressive imaging and passive remote sensing.

Some embodiments provide methods for measuring one or more sinusoidal Fourier components of an object. The methods include generating a structured second radiation by spatially modulating a first radiation. The structured second radiation illuminates the object. The structured second radiation is scaled and oriented relative to the object. The object produces a third radiation in response to being illuminated. A single-element detector detects a portion of the third radiation from multiple locations on the object substantially simultaneously for each spatial modulation of the first radiation and for each orientation of the second radiation. A time-varying signal is produced based on the detected portion of the third radiations. One or more characteristics of the one or more sinusoidal Fourier components of the object are estimated based on the time-varying signal.

Some embodiments provide systems for measuring one or more sinusoidal Fourier components of an object. The systems include a spatial modulator to spatially modulate a first radiation to produce a structured second radiation that illuminates the object. The systems also include a single-element detector positioned to receive radiation from multiple locations on the object substantially simultaneously for each spatial modulation of the first radiation and for each orientation of the second radiation to produce a time-varying signal. A computational unit in communication with the single-element detector is included in the system. The computational unit includes instructions to determine at least one characteristic of the one or more sinusoidal Fourier components of the object based on the time-varying signal.

Other embodiments provide additional systems for measuring one or more sinusoidal Fourier components of an object. The systems include means for producing a structured second radiation by spatially modulating a first radiation. Means for illuminating the object with the structured second radiation are also included. The structured second radiation is also oriented and scaled with respect to the object. The systems also include means for detecting a third radiation received from multiple locations on the object substantially simultaneously for each spatial modulation of the first radiation and for each orientation of the second radiation. A means for producing a time-varying signal based on the detected third radiation are included. The system also includes a means for processing the time-varying signal to determine at least one characteristic of the one or more sinusoidal Fourier components of the object.

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following the reference label by a hyphen and a second label or third label that distinguishes among the similar components. The second or third label may also be used merely to distinguish components that are part of different figures. If the first reference label is used in the specification, the description is applicable to any one of the similar components having the same first reference label irrespective of the second reference or third labels.

DETAILED DESCRIPTION

This description provides example embodiments only, and is not intended to limit the scope, applicability, or configuration of the invention. Rather, the ensuing description of the embodiments will provide those skilled in the art with an enabling description for implementing embodiments of the invention. Various changes may be made in the function and arrangement of elements without departing from the spirit and scope of the invention.

Thus, various embodiments may omit, substitute, or add various procedures or components as appropriate. For instance, it should be appreciated that in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner.

It should also be appreciated that the following systems, methods, and software may individually or collectively be components of a larger system, wherein other procedures may take precedence over or otherwise modify their application. Also, a number of steps may be required before, after, or concurrently with the following embodiments.

Figure 1:
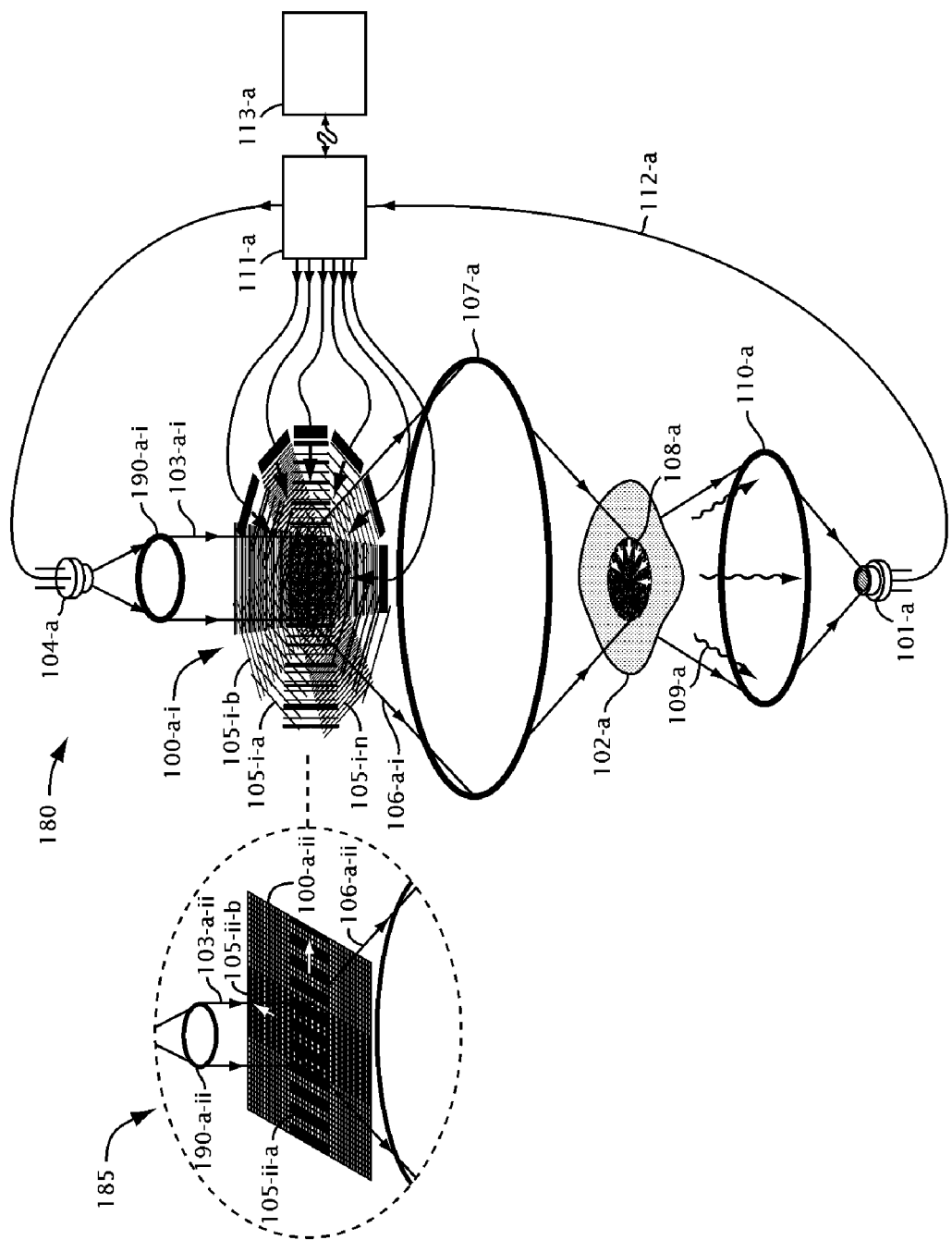
FIG. 1 illustrates a system where an object may be illuminated with a radiation wavefront that has been spatially modulated in two-dimensions using multiple moving sinusoidal patterns and radiation transmitted by the object in response to the illumination is detected with a single-element detector, in accordance with various embodiments.

FIG. 1 illustrates a Fourier domain sensing system 180, in accordance with various embodiments. By using a two-dimensional spatial illumination modulator 100-$a$, the system 180 makes it possible to measure multiple complex Fourier components of the object along multiple dimensions simultaneously using a single-element detector 101-$a$. This data may be used to measure a characteristic of the object 102-$a$, such as its position, shape, or orientation, to classify the object, or to reconstruct an image of the object, merely by way of example. The system may provide, without limitation, parallel high-speed data acquisition without moving components, flexible and configurable Fourier domain sampling, high dynamic range sensing using a single-element detector, simplicity, and/or compatibility with existing spatial light modulator technologies.

In some embodiments, radiation 103-$a$-$i$ emitted by a radiation source 104-$a$ may be modulated in phase, amplitude, wavelength, and/or polarization using a two-dimensional spatial modulator 100-$a$ that may be programmed with a dynamic pattern that can be considered as a combination of moving sinusoidal components 105-$i$-$a$, 105-$i$-$b$, ..., 105-$i$-$n$. In some embodiments, a lens 190-$a$-$i$ may collimate radiation 103-$a$-$i$. In the case of polarization modulation, a polarization analyzing element may be used to convert polarization modulation to intensity modulation. The spatially modulated illumination 106-$a$ may then be projected onto the object 102-$a$ using a projection optical system 107-$a$, such as a lens, thereby illuminating the object 102-$a$ with a combination of dynamic sinusoidal patterns 108-$a$. Radiation 109-$a$ scattered, reflected, transmitted, generated, and/or fluoresced by the object 102-$a$ in response to the structured illumination 108-$a$ may be collected over a substantial range of angles using a detection optical system 110-$a$, such as a lens, onto a single-element detector 101-$a$. An electronic control system 111-$a$ may be used to program the spatial modulator 100-$a$, acquire a time-varying detector signal, and/or optionally amplitude-modulate the radiation source 104-$a$ in order to convert the time-varying detector signal 112-$a$ to a more accessible range of frequencies. A processor and/or computational device 113-$a$ in communication with the control system 111-$a$ may be used to process the acquired detector signal to compute the Fourier components of the object. The computed Fourier components of the object may be used for a wide variety of purposes including, but not limited to using this information to characterize the object 102-$a$ and/or reconstruct its image, as is discussed in more detail below.

In some embodiments, each moving sinusoidal component 105-$i$-$a$, 105-$i$-$b$, ..., 105-$i$-$n$ present in the dynamic spatial modulation pattern may be characterized by a unique combination of spatial frequency, amplitude, spatial phase, direction, and/or equation of motion, and may produce a corresponding moving sinusoidal illumination component at the object with a linearly-related set of characteristics. In one embodiment, each such illumination component may vary sinusoidally in intensity and may move with a constant velocity across the object. By representing the intensity response of the object as an integral sum of its Fourier components, multiplying by the moving sinusoidal intensity pattern, and spatially integrating, a detector signal may be written as the following Equation 1:

$$I_d(t) = I_i \int\int_\infty^\infty \left[\int\int_\infty^\infty A_r(f_x, f_y)e^{j2\pi(f_x x + f_y y)} df_x df_y\right] \cdot \left[1 + \frac{m}{2}e^{j2\pi(f_{0x}x - v_0 t)} + c.c.\right] dx dy = I_i\left(A_r(0,0) + \frac{m}{2}A_r(f_{0x}, 0)e^{j\pi v_0 t} + c.c.\right)$$

Here $A_r(f_x, f_y)$ represents the complex Fourier transform of the intensity response of the object encompassed by the finite illumination area, $I_i$ and $I_d$ are the incident and detected intensities, $f_{0x}$ and $v_0$ are the spatial and temporal frequencies of the illumination, m is the modulation depth, and c.c. represents the complex conjugate. Thus, the spatially-integrated flux 109-$a$ scattered, reflected, transmitted, generated, and/or fluoresced by the object 102-$a$ that may be illuminated by a moving sinusoidal pattern may oscillate in time, wherein the amplitude and/or phase of the oscillation may correspond to the strength and/or offset of the matching Fourier component present in the intensity response of the object 102-$a$. The combined detector signal 112-$a$ due to the linear sum of moving sinusoidal illumination components 108-$a$ may then be represented as a linear sum of time-varying sinusoidal signals, where the temporal frequency of each sinusoidal signal may be related to the corresponding spatial frequency in the object's illumination response as $v_0 = v_x f_{0x}$, where $v_x$ is the velocity of motion of the sinusoidal illumination. Therefore, individual Fourier components of the object may be recovered by time-domain Fourier analysis of the frequency-multiplexed detector signal 112-$a$. In one embodiment, where each moving sinusoidal spatial modulation component 105 may be used to measure a unique Fourier component of the object, the product of the velocity and spatial frequency of said spatial modulation component may be chosen to be unique.

It should be apparent to those skilled in the art that a variety of implementations of said embodiments is possible within the spirit and scope of this invention. The radiation 103-*a-i* may be visible and/or invisible, particulate and/or wavelike, and may be temporally and/or spatially coherent, as in the case of laser radiation, and/or partially coherent, as in the case of radiation from a Light Emitting Diode (LED). The two-dimensional spatial modulator 100-*a* may be transmissive and/or reflective and may take the form of a programmable grid of elements, such as a Liquid-Crystal (LC) array or a Digital Micromirror Device (DMD), a continuous structured medium, and/or a deformable surface or membrane. In one embodiment, the two-dimensional spatial modulator 100-*a* may include a radial combination of one-dimensional spatial modulators. Merely by way of example, system 180 may show an embodiment where a body of water perturbed by ultrasonic waves emanating from multiple actuators arranged at the periphery may be used as a two-dimensional spatial modulator 100-*a-i*, which may produce multiple moving sinusoidal components 105-*i-a*, 105-*i-b*, . . . , and 105-*i-n*. In some embodiments, the two-dimensional spatial modulator 100-*a* may include multiple one-dimensional spatial modulators, which may include but are not limited to a one-dimensional acoustic optic Bragg cell, a surface acoustic wave device, and/or a programmable grating device, such as grating light valve device. As another example, subsystem 185 shows an embodiment where a two dimensional LC array or DMD array 100-*a-ii* is programmed to produce multiple moving sinusoidal components such as 105-*ii-a* and 105-*ii-b* as part of the two-dimensional spatial modulator 100-*i*. The two-dimensional spatial modulator 100-*a-ii* may spatially modulate radiation 103-*a-ii*. Lens 190-*a-ii*. may also collimate radiation 103-*a-ii*. Although the preceding discussion treated an object illuminated with an intensity pattern, other spatially-varying properties of the illumination, such as polarization and/or wavelength, may also be used to probe structure present in the object 102-*a*. Furthermore, although a substantial portion of radiation 109-*a* coherently scattered by the object may typically be collected onto the detector 101-*a* to spatially integrate any localized structure present in the response, such as speckle, when radiation 109-*a* from the object 102-*a* is isotropic only a small portion may need to be collected. For example, in the case of a strong fluorescent response, the detection optical system 110-*a* may not be needed and a bare spectrally-filtered detector element 101-*a* positioned in relative proximity to the object 102-*a* may be sufficient to perform high-fidelity Fourier-domain measurements using these techniques.

Figure 2:
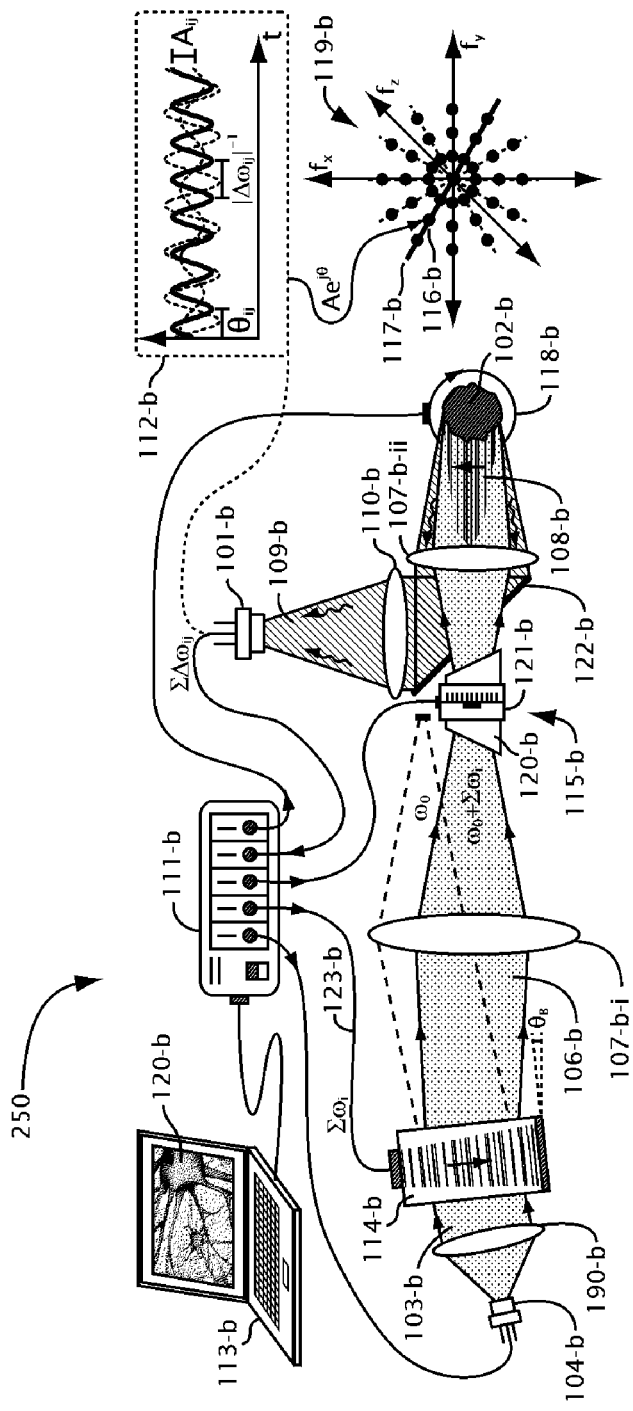
FIG. 2 illustrates a system where an image of an object may be reconstructed by illuminating the object with a radiation wavefront that has been spatially modulated with multiple moving sinusoidal patterns using an acousto-optic Bragg cell and rotated using a prism, detecting the scattered, reflected, transmitted, fluoresced, or otherwise generated response with a single-element detector, and computing the image from the measured Fourier components using a processor, in accordance with various embodiments.

FIG. 2 illustrates a Fourier domain sensing system 250, in accordance with various embodiments. The system 250 shows an object 102-*b* that may be illuminated with structured illumination 108-*b* generated using a one-dimensional spatial modulator 114-*b* and a wavefront rotating device 115-*b*. While it is possible to measure multiple Fourier components 116-*b* simultaneously along a single direction in this embodiment, other directions or radial "slices" 117-*b* in Fourier space may be accessed sequentially. Furthermore, the object 102-*b* itself may be rotated or tilted using a mechanical stage 118-*b* to measure different Fourier slices in the three-dimensional Fourier space 119-*b*, from which a two- or three-dimensional object characteristic or image 120-*b* can be reconstructed. Due to the availability of high-speed one-dimensional spatial modulators, Fourier measurements may be acquired very rapidly in some embodiments, especially when a non-mechanical wavefront rotating device 115-*b* may be used. Whereas parallel acquisition of multiple Fourier components 116-*b* along a Fourier slice 117-*b* may increase measurement speed, sequential acquisition of individual Fourier samples may make it possible to attain a very large Depth of Field, which is substantially limited by the extent of axial invariance of the illumination pattern 108-*b*. During sequential measurements of individual Fourier components, the axial extent of the sinusoidal interference patterns illuminating the object may be very large, which may make it possible to attain a millimeter-scale Depth of Field while maintaining wavelength-scale resolution, merely by way of example.

In one embodiment, radiation 103-*b* emitted by a radiation source 104-*b* with optical frequency $\omega_0$ may be collimated using a lens 190-*b* and spatially modulated using a one dimensional spatial modulator 114-*b*. Merely by way of example, the one dimensional spatial modulator may be an acousto-optic Bragg cell. The diffracted $1^{st}$ order radiation wavefront 106-*b* may be rotated using a prism 120-*b*, such as a Dove prism, and/or an arrangement of mirrors mounted on a rotation stage 121-*b*, and projected onto the object 102-*b*. In some embodiments, other diffraction orders may also be utilized. System 250 may include one or more lenses, such as 107-*b-i* and 107-*b-ii*, which may be used to facilitate projecting wavefront 106-*b* onto the object 102-*b*. In some embodiments, other diffraction orders of the radiation may be utilized. Radiation 109-*b* scattered, reflected, transmitted, fluoresced, or otherwise generated by object 102-*b* in response to the structured illumination 108-*b* may be directed by means of a beam splitter 122-*b* and additional optics, such as lens 110-*b* onto a single-element detector 101-*b*. An electronic control system 111-*b* may be used to program the one dimensional spatial modulator 114-*b*, control a combination of wavefront and object rotation stages 121-*b*, 118-*b*, acquire the time-varying detector signal 112-*b*, and/or optionally amplitude-modulate the radiation source 104-*b* in time in order to convert the time-varying detector signal 112-*b* to a more accessible range of frequencies. A processor 113-*b* in communication with the control system 111-*b* may used to process the acquired detector signal 112-*b* to compute the Fourier components 116-*b* of the object 102-*b* and use this information to characterize the object and/or reconstruct its image 120-*b*, merely by way of example.

In one embodiment, the one dimensional spatial modulator 114-*b* such as a Bragg cell, for example, may be driven with a compound electronic signal 123-*b* comprising multiple sinusoidal waveforms. Each sinusoid waveform may be described by a combination of amplitude, phase, and/or temporal frequency, such that at any time the drive signal can be characterized by a combination of frequencies, $\Sigma\omega_i$. A piezo-electric transducer (part of Bragg cell 114-*b*) converts the electronic signal into an acoustic waveform, which perturbs the index of refraction of the Bragg cell crystal (part of Bragg cell 114-*b*) via the photoelastic effect, resulting in a one-dimensional volume phase hologram traveling through the Bragg cell crystal at the velocity of sound. To maximize diffraction efficiency, the radiation may enter the Bragg cell 114-*b* at an angle with respect to the acoustic velocity normal substantially close to the Bragg angle, $\theta_B$. Furthermore, the Bragg cell 114-*b* may be driven sufficiently weakly so that the diffraction efficiency varies substantially linearly with the electronic drive signal power. Due to the acousto-optic Doppler effect, radiation diffracted by each spatial frequency present in the traveling volume hologram may acquire a corresponding temporal frequency shift, such that the $1^{st}$ order diffracted radiation wavefront 106-*b* may be characterized by a combination of frequencies, $\omega_0+\Sigma\omega_i$. Furthermore, each spatial frequency present in the hologram may diffract light at a different angle, resulting in a compound interference pattern 108-*b* that can be considered as a combination of sinusoidal intensity patterns moving across the object 102-*b*, where the spatial frequency of each sinusoid may be linearly related to the corresponding temporal difference frequency $\Delta\omega_{ij}$, present in the electronic drive signal 123-b. In this way, patterns present in the moving volume hologram may be projected onto the object 102-b.

As in the case of the embodiment illustrated in FIG. 1 and described earlier, each moving sinusoidal intensity component present in the illumination 108-b may produce an oscillating signal contribution at the detector 101-b, such that the compound detector signal 112-b can be characterized by a combination of frequencies, $\Sigma\Delta\omega_{ij}$. The amplitude, $\Delta_{ij}$, and phase, $\theta_{ij}$, of each oscillating signal component may correspond to the magnitude and phase of the corresponding spatial Fourier coefficient 116-b of the object 102-b. In this way, multiple Fourier components of the object 102-b can be measured simultaneously and recovered by time-domain Fourier analysis of the frequency-multiplexed detector signal. In one embodiment, where each acoustic beat pattern in the Bragg cell 114-b may be used to measure a unique Fourier component of the object, the difference frequencies $\Delta\omega_{ij}$, present in the Bragg cell drive signal 123-b may be chosen to be unique.

It should be apparent to those skilled in the art that a variety of implementations of the embodiment in FIG. 2 are possible within the spirit and scope of this invention. For example, the one-dimensional spatial modulator 114-b may be reflective, as in the case of a Surface Acoustic Wave (SAW) device or a programmable grating device, such as Grating Light Valve (GLV) device. Some embodiments may also utilize a two-dimensional modulator as discussed with respect to FIG. 1. The wavefront rotation device 115-b may also be reflecting, including a retro-reflecting prism and/or an arrangement of mirrors, or may be implemented without moving components so that the illumination can be rotated faster than the acoustic propagation time across the optical aperture. In the latter case, sequential measurements of Fourier components may be accomplished by rotating the illumination for each position of the illumination pattern before varying the spatial frequency, rather than the other way around. Measurements along different Fourier slices 117-b can be accomplished by rotating the illumination, rotating or tilting the object 102-b, or any combination of these techniques. To improve signal contrast, the beam splitter 122-b that may be used to separate radiation 109-b due to the object from the illumination 108-b may be polarizing when the object response is scattered, or dichroic when the response is fluoresced. Due to the nearly common path of the diffracted beams, the radiation may be temporally and spatially coherent, as in the case of laser radiation, or partially coherent, as in the case of radiation from a Light Emitting Diode (LED), merely by way of example.

Fourier Optics can be used to derive the dynamic Optical Transfer Function (OTF) of the illustrated system 250 and the other systems illustrated with in other figures. Consider the effect of an arbitrary RF drive signal 123-b, s(t), on the detected intensity 112-b, $I_d(t)$, under coherent illumination. When the Bragg cell 114-b is operated in the linear regime, the incident field 103-b is modulated along the y' axis by the propagating acoustic pattern in proportion to the time-delayed RF signal 123-b, convolved in time with the acousto-optic impulse response, $h_a(t)$, and windowed by the optical and acoustic beam overlap cross-section, a(x',y'), which is reflected in the following Equation 2:

$$U_a(x', y', t) = a(x', y')\left[h_a(t) * s(t) * \delta\left(t - \frac{t_a}{2} + \frac{y'}{v_s}\right)\right]e^{j\omega t} + c.c.$$

where $v_s$ is the speed of sound in the crystal, and w is the optical frequency. Before illuminating the object, the diffracted field 106-b is convolved with the one-dimensional impulse response of the projection system, p(y), and demagnified by a factor M. The resulting interference pattern 108-b is then multiplied by the object's 102-b intensity response, $|\sigma(x,y)|^2$, and spatially integrated at the detector 101-b. The detected signal may be represented as the following Equation 3:

$$I_d(t) = \int\int_{-\infty}^{\infty} |\sigma(x, y)|^2 \cdot \left|p(y) * \left[a(Mx, My)s_a\left(t - \frac{t_a}{2} + \frac{My}{v_s}\right)\right]\right|^2 dy\,dx$$

where $s_a(t,y)$ represents the term in the brackets in Equation 2. One may now apply a time-domain Fourier transform and obtain the following Equation 4:

$$\mathcal{F}_t\{I_d(t)\} = e^{j\pi v t_a} \int\int_{-\infty}^{\infty} |\sigma(x, y)|^2 \cdot$$

$$\mathcal{F}_y\left\{\left|p(y) * \left[a(Mx, My)s_a\left(\frac{My}{v_s}\right)\right]\right|^2\right\}e^{-j2\pi v My/v_s} dy\,dx.$$

where $\mathcal{F}_y\{\ \}$ represents a one-dimensional slice through the spatial Fourier transform. Converting from temporal to spatial frequency using $v=f_y v_s/M$ in post-processing, moving the $\mathcal{F}_y\{\ \}$ term outside the integral, and recognizing the integral as another Fourier slice, one may obtain the one-dimensional optical transfer function, represented in the following Equations 5A and 5B:

$$OTF^{1D}(f_y) = \frac{\mathcal{F}_y\{|\sigma_r(x, y)|^2\}}{\mathcal{F}_y\{|\sigma(x, y)|^2\}} = e^{j\pi f_y v_s t_a f/M} \cdot \{\mathcal{H}(f_y) * \mathcal{H}(f_y)\}$$

$$\mathcal{H}(f_y) = \mathcal{P}(f_y) \cdot \left[A\left(\frac{f_y}{M}\right) * S_a\left(\frac{v_s f_y}{M}\right)\right]$$

Here $\mathcal{F}_y\{|\sigma_r(x,y)|^2\}$ is a Fourier slice of the reconstructed object, ★ stands for correlation, and $P(f_y)$, $S_a(f_y)$, and $A(f_y)$ are one-dimensional Fourier transforms of p(y), $s_a(y)$, and the projection of a(x,y), respectively. One can see from this result that electronic control of the RF signal allows adjustment of the $OTF^{1D}$ of the system on a slice-by-slice basis. By applying the Fourier Slice Theorem, one can thereby synthesize a dynamic two- or three-dimensional OTF and obtain a reconstruction of the object using the following Equations 6A and 6B:

$$OTF^{2D}(f_x, f_y) = W(f_x, f_y) \int_0^\pi OTF_0^{1D}(f_x \sin\theta + f_y \cos\theta) d\theta$$

$$|\sigma_r(x, y)|^2 = \mathcal{F}^{-1}_{f_x \cdot f_y}\{OTF^{2D}(f_x \cdot f_y)\mathcal{F}_{x,y}\{|\sigma(x, y)|^2\}\}$$

where $\theta$ is the Fourier slice angle and $W(f_x, f_y)$ is an angle-independent weighting filter accounting for sparser sampling of Fourier space at higher frequencies. In conjunction with a feedback system, it may thus be possible, for example, to dynamically correct coarse phase errors in the pupil function (e.g. due to flexing of a large reflector), and/or to adapt the OTF to a changing scene. The dynamic OTF also may enable Fourier-domain filtering in real time and without the loss of light associated with amplitude-mask-based filtering. This capability may not be only helpful for optical processing applications, but may also be used to optimize imaging sensitivity or measurement time based on a priori information about the Fourier content of a class of objects, such as thin cellular membranes or grid-based semiconductor structures, enabling a form of compressive imaging.

Figure 3A:
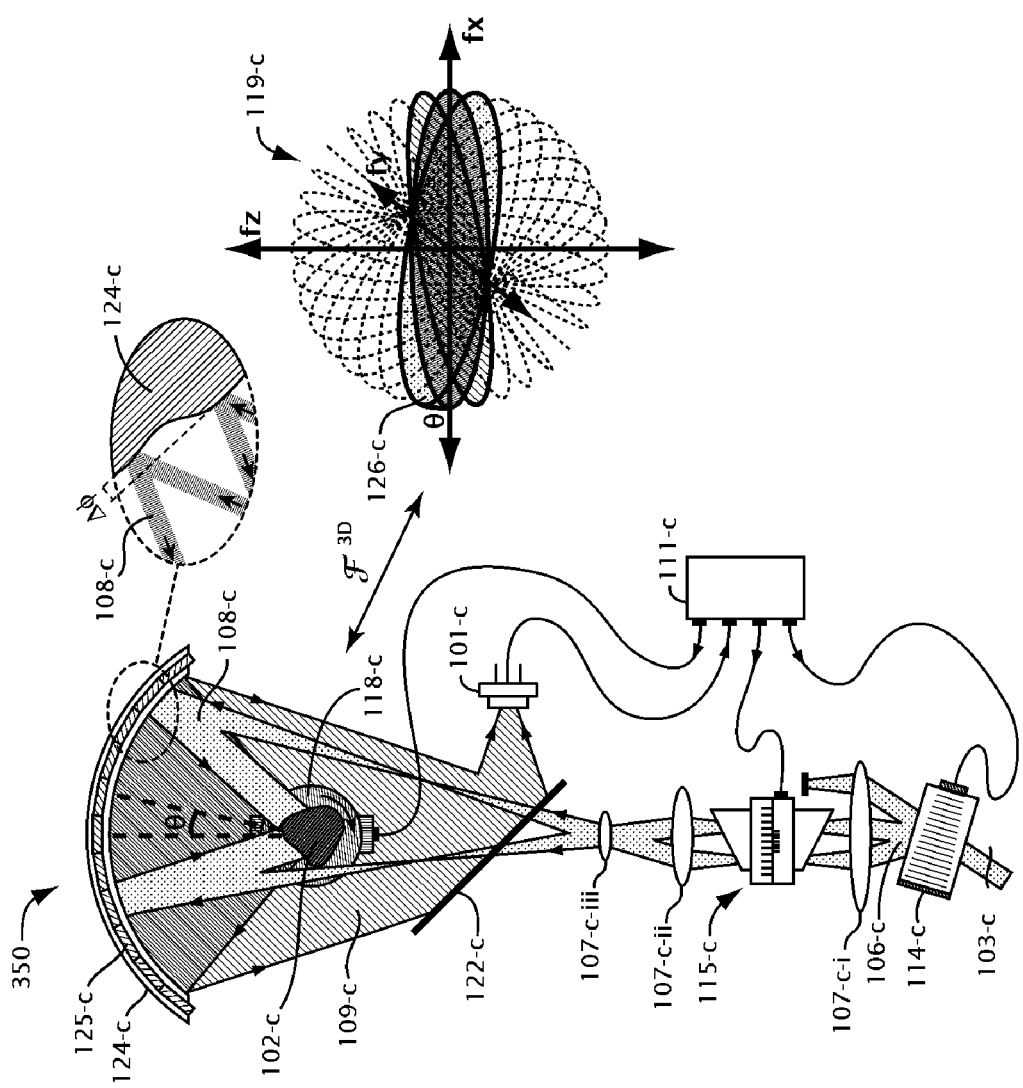
FIG. 3A illustrates a system that may be used for measuring tilted planes in Fourier space and probing three-dimensional structures by tilting the object and/or tilting the illumination and using an electronically phase-compensated large low-precision reflector to project structured illumination and collect the object's scattered, reflected, transmitted, fluoresced, or otherwise generated response onto a single-element detector, in accordance with various embodiments.

FIG. 3A illustrates an embodiment of another Fourier domain sensing system 350, in accordance with various embodiments. System 350 includes a reflector 124-*c*, which may be a large, low-precision reflector. Reflector 124-*c* may be used to project the illumination 108-*c* and collect the scattered, reflected, transmitted, fluoresced, or otherwise generated radiation 109-*c* from the object 102-*c* onto a single-element detector 101-*c* via a dichroic or polarizing beam splitter 122-*c*. Such a large aberration-compensated reflector can be many centimeters in diameter and can be positioned many centimeters or even meters away from the object, while maintaining wavelength-scale resolution and millimeter-scale depth of field. The reflector surface 124-*c* may need to be optically-precise only within a small fraction of its Numerical Aperture (NA), where this fraction is approximately the inverse of the number of resolvable spots, or equivalently, the time-bandwidth product of the Bragg cell 114-*c*, which can exceed several thousand. Coarser phase errors, $\Delta\phi$, in the reflecting surface, however, may be corrected by electronically adjusting the phase of the acoustic waveform or in post-processing. A calibration step may be performed to measure the phase errors by temporarily replacing the object with a known target such as a small fluorescent bead, a combination of gratings, or a Fresnel zone plate. Alternatively, known constraints about the object itself may be used to extract the phase errors in the reflector surface. The reflector may be machined out of metal, electroformed, or even assembled from a mosaic of flat mirrors 125-*c*. In one embodiment, the reflector surface may be ellipsoidal, with one of the foci located at the object, and the other at a spatial modulation conjugate plane. In one embodiment, the reflector 124-*c* may include multiple mirror segments that can be folded for storage.

Also illustrated is an embodiment wherein it is possible to measure individual Fourier components in three dimensions, from which a three-dimensional image can be reconstructed. As described earlier, by rotating the illumination pattern or the object itself about the illumination axis or by using a two-dimensional spatial modulator, it is possible to measure Fourier components of the object lying on a plane in the three-dimensional Fourier space 119-*c*. Additional tilted Fourier planes such as 126-*c* can be measured by tilting the object using a mechanical stage 118-*c* and/or by tilting the illumination axis, which can be accomplished, for example, through rapid electronic control of the center frequency of the signal driving the one dimensional spatial modulator such as Bragg cell 114-*c*. While the range of illumination axis tilts θ may be limited by the NA of the projection system, as illustrated in Fourier space using heavy lines of Fourier space 119-*c*, by tilting the object it is possible to fully sample the three-dimensional Fourier space, as illustrated by tilted Fourier planes with dotted lines of Fourier space 119-*c*. It should be apparent to those skilled in the art that it is not necessary to measure one plane at a time in Fourier space. The operations of rotating and tilting the object with respect to the illumination pattern may be performed in any sequence to build up the desired three-dimensional distribution of Fourier samples.

Figure 3B:
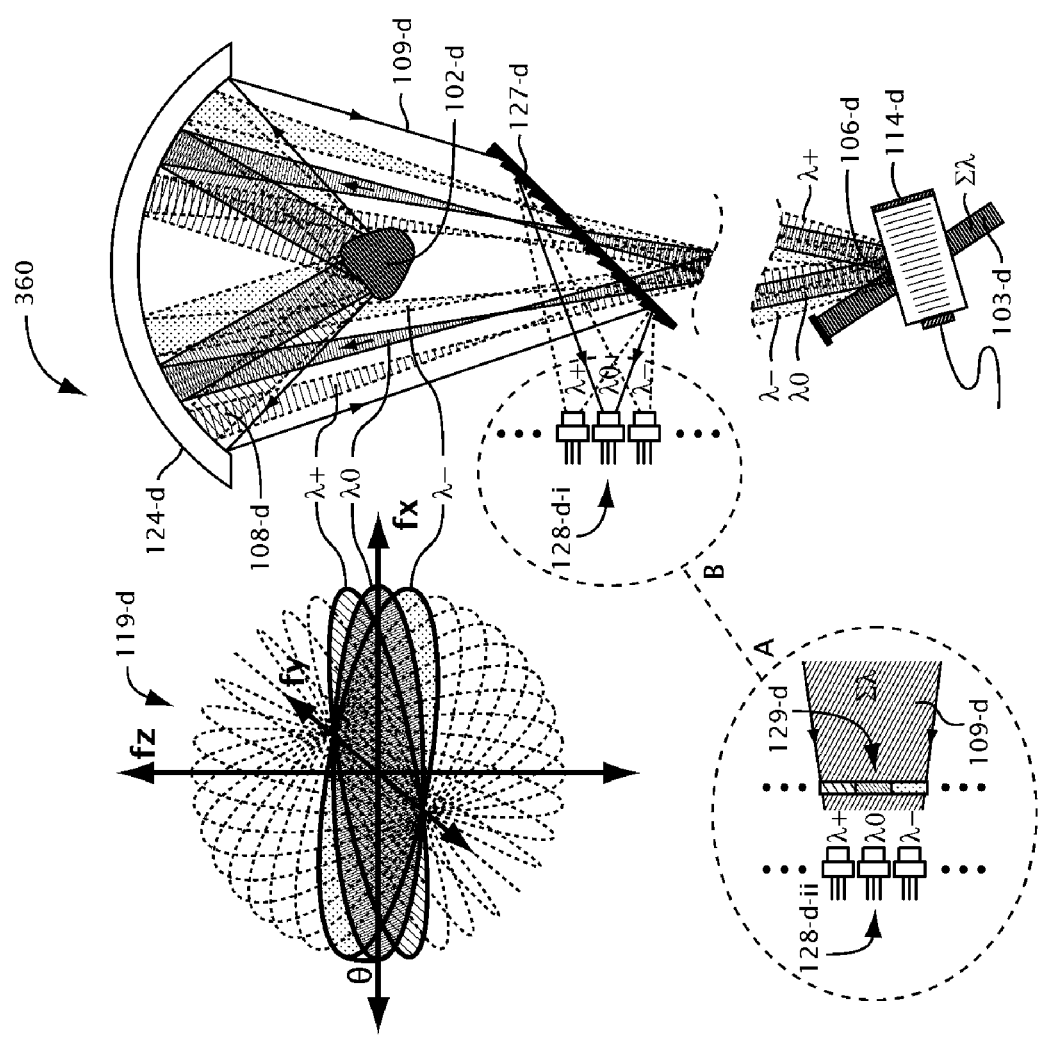
FIG. 3B illustrates a system that may be used for measuring tilted planes and/or slices in Fourier space and probing three-dimensional structures by using spectrally distributed illumination, dispersive elements and/or filters, and multiple detectors to measure multiple groups of Fourier components in parallel using different wavelengths.

FIG. 3B illustrates another embodiment of a Fourier domain sensing system 360 where three-dimensional Fourier slices or planes having different tilts may be measured simultaneously using a source of broadband radiation 103-*d*, rather than by sequentially tilting the object or the illumination axis. This parallel spectrally-multiplexed technique may greatly speed up the acquisition of three-dimensional images. In this embodiment, the spatial modulator 114-*d* may impart different diffraction angles onto different spectral components of the modulated radiation 106-*d*, three of which are labeled in increasing order of wavelength as $\lambda-$, $\lambda 0$, and $\lambda+$. As a result, the axis of illumination 108-*d* due to each spectral component may be unique, thereby mapping different tilts of Fourier slices or planes to different illumination wavelengths. When the signal from the object 109-*d* is due to scattered light, signals from spectrally-coded loci in Fourier space can be separated using a dispersive element 127-*d*, such as a grating, onto an array of detectors 128-*d-i*. Alternatively, a bank of spectral filters 129-*d* placed in front of a detector array 128-*d-ii* can be used instead of a dispersive element. When the detected signal is due to fluorescence, the object can be labeled with a combination of fluorophores with substantially non-overlapping absorption spectra to separate signals due to different components of the illumination spectrum.

It should be apparent to those skilled in the art that a variety of implementations of the embodiment in FIGS. 3A and 3B are possible within the spirit and scope of this invention, including such variations as are seen with embodiments of FIG. 1 and FIG. 2. Furthermore, various components of FIGS. 3A and 3B may be labeled with first reference numbers that may be described above along with FIGS. 1 and/or 2. A second label on a component may merely reflect that the component is part of a specific figure.

Figure 4:
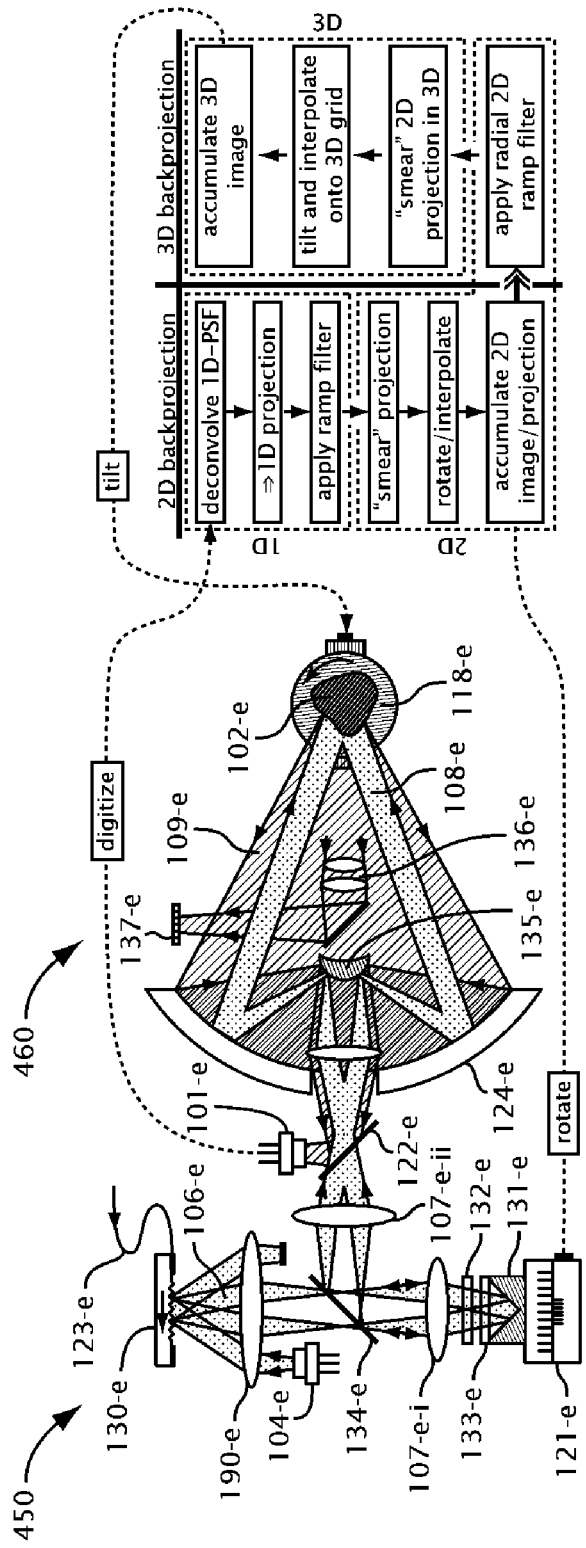
FIG. 4 illustrates a system wherein illumination spatially modulated using a reflecting Surface Acoustic Wave device and rotated using a retro-reflecting prism or mirror arrangement may be projected onto the object using an in-line reflector system, the object's response is detected with a single-element detector, and a two- or three-dimensional image is reconstructed using the tomographic filtered backprojection algorithm in real time or in post-processing, in accordance with various embodiments.

FIG. 4 illustrates another Fourier domain sensing system 450, in accordance with various embodiments. In system 450, illumination patterns may be generated using a reflective Surface Acoustic Wave (SAW) device 130-*e*, rotated using a retro-reflecting right-angle prism or mirror arrangement 131-*e*, and projected onto the object using a large low-precision reflector 124-*c*. The SAW device 130-*e*, which may be fabricated by patterning an inter-digitated transducer and depositing a reflective surface on a Lithium Niobate wafer in some embodiments, is functionally similar to the acousto-optic Bragg cell described earlier. However the propagating acoustic waves of the SAW device may perturb the shape of a reflecting surface rather than the index of refraction in a bulk crystal as with an acousto-optic Bragg cell. Because SAW perturbations are typically only a small fraction of the optical wavelength, diffraction efficiency may be much lower than in the case of the volume-holographic Bragg cell. A SAW device 130-*e* can be inexpensive to manufacture, does not require Bragg-matching, and can work in wavelength regimes where acousto-optic crystals are not available, including UV and X-rays. The retro-reflecting illumination rotator 131-*e* may be easier to align than a transmissive one such as a Dove prism, may introduce fewer aberrations, and when implemented using mirrors may work in wavelength regimes where prisms may not be available. As with a transmissive prism, the illumination pattern is rotated by the retro-reflector 131-*e* at twice the rate of the rotation stage 121-*e*. Since a Fourier plane can be fully sampled with 180 degrees of rotation, the stage revolution rate may be quadrupled when calculating the image acquisition rate. A pair of retarders, one 132-*e* stationary and the other 133-*e* that may be mounted on the rotation stage, can be used to preserve the linear polarization state as the pattern is rotated, which may maximize the coupling efficiency of the beam splitter 134-*e*, which may be polarizing. In this embodiment, the fixed quarter-wave retarder 132-*e* is used to turn the incoming linear polarization into circular, while the other rotating retarder 133-*e*, its fast axis aligned with the edge of the right-angle prism or mirrors, is used to nullify the polarization effects of the retro-reflector so that polarization behavior of the rotating elements taken together is that of a mirror and the system functions as an optical isolator.

The diffracted and rotated $1^{st}$-order radiation 106-c from the SAW device 130-e may be coupled into the projection system 460 via a small central aperture in the large reflector 124-e and may be directed back onto the reflector 124-e via a secondary mirror 135-e, which magnifies the diffraction angle. In some embodiments, other diffracted orders of the radiation 106-e may also be utilized. As in FIGS. 3A and 3B, radiation from the object 109-c in response to the illumination 108-e may be collected using the same reflector 124-e and directed onto a single-element detector 101-e via beam splitter 122-e, which may be dichroic or polarizing. In one embodiment, the reflector 124-e may be ellipsoidal in shape, with one of its foci located at the object 102-e and the other coinciding with the focus of the paraboloidal secondary mirror 135-e. In some embodiments, a miniature optical system 136-c may be placed just behind the secondary mirror 135-e to form a low-resolution image onto an imaging detector array 137-e such as a CCD. This low resolution image can then be combined with the reconstructed high resolution image to fill in the low spatial frequencies that would otherwise be lost due to shadowing by the secondary mirror, while still maintaining a large depth of field. Furthermore, the imaging detector 137-e and optical system 136-e may be the primary imaging instrument, whereas the Fourier domain sensing system 450 may be used as a means to enhance the resolution of the optical system 136-e. Moreover, in addition to direct acquisition of low-resolution images, the imaging detector 137-e can also be used instead of or in addition to the single-element detector 101-e to capture and to spatially integrate a portion of the object radiation 109-e emitted or scattered in response to the structured illumination 108-c. This can be accomplished by summing the signals from multiple detector elements comprising the imaging detector array in some embodiments.

Also illustrated is a method for reconstructing an image of the object from the time-domain detector signal that may be utilized with embodiments such as system 450. As described above, the one-dimensional Optical Transfer Function (OT-$F^{1D}$), and therefore the one-dimensional point spread function (PSF$^{1D}$), of the system may be determined by the RF signal 123-e driving the acousto-optic spatial modulator 130-e. For each measured Fourier slice, by deconvolving the digitized detector signal with the PSF$^{1D}$, a one-dimensional projection of the object may be obtained along the lateral direction normal to the Fourier slice. A two-dimensional image can be reconstructed by applying the Filtered Backprojection (FBP) algorithm, a method commonly used in the field of projection tomography to reconstruct a two-dimensional image from multiple one-dimensional projections. The image may be obtained using this algorithm by filtering each one-dimensional projection using a ramp filter to compensate for sparse Fourier sampling at high spatial frequencies, smearing the filtered projection in two dimensions along the projection direction, and coherently accumulating the smeared projections. Unlike rectilinear direct Fourier transform techniques, this process can be performed entirely in real space potentially resulting in fewer interpolation artifacts, and makes it possible to synthesize the image in real time, slice-by-slice, rather than in post-processing. Furthermore, because the Fourier Slice Theorem applies in three as well as two dimensions, the FBP algorithm may be extended straightfowardly to reconstruct a three-dimensional image from measurements mapping to multiple tilted planes in Fourier space, such as those shown in FIG. 3. Because this tomographic approach to three-dimensional imaging can be sensitive to radiation emitted from locations within the entire illumination volume, it can be more light-efficient than confocal optical sectioning techniques in which out-of-focus light is rejected.

It should be apparent to those skilled in the art that a variety of implementations of the embodiment in FIG. 4 are possible within the spirit and scope of this invention, including such variations as are seen with embodiments of FIGS. 1, 2, 3A, and 3B. Furthermore, various components of FIG. 4 may be labeled with first reference numbers that may be described above along with FIGS. 1, 2, 3A, and/or 3B. A second reference label on a component may merely reflect that the component is part of a specific figure.

Figure 5:
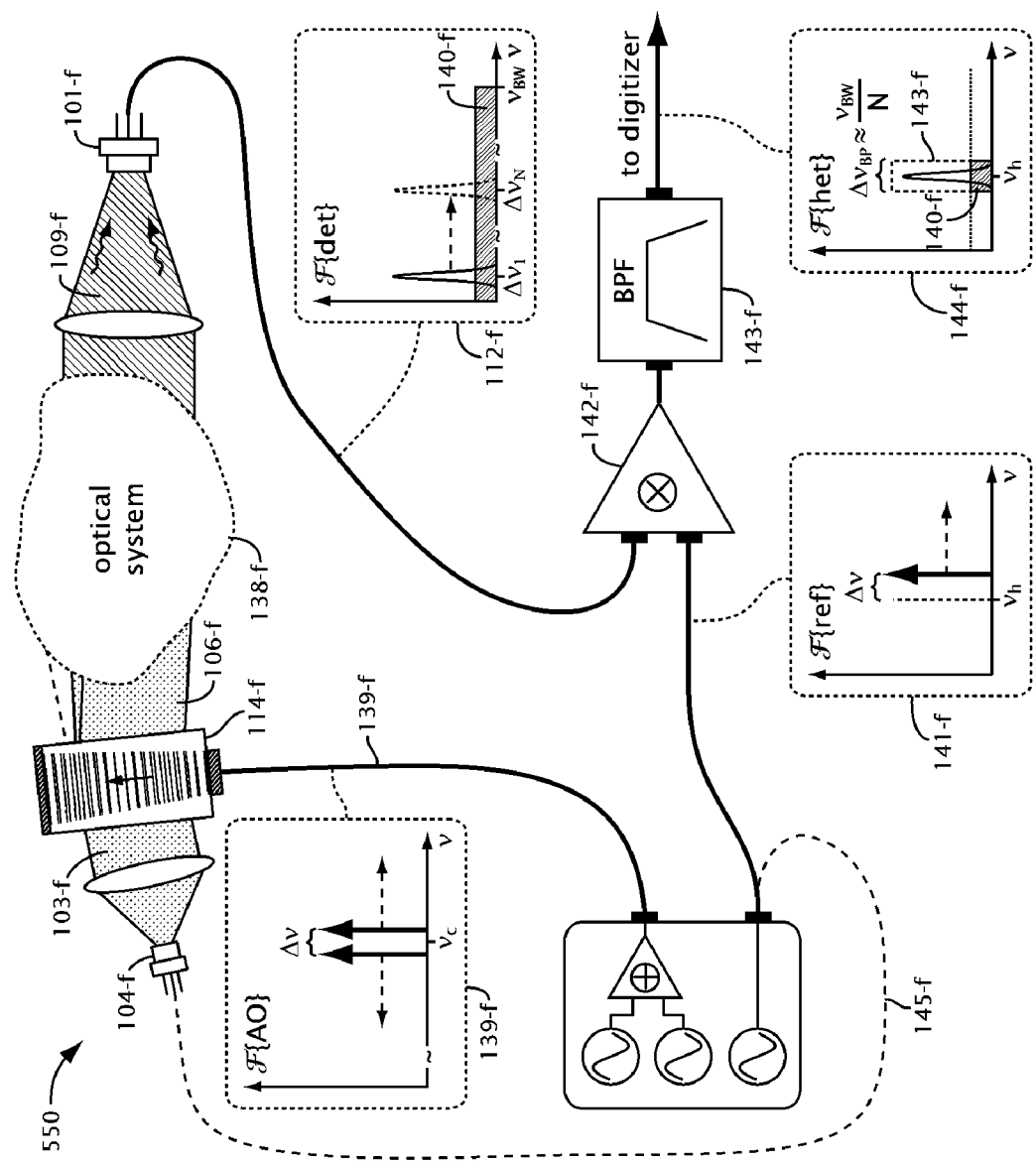
FIG. 5 illustrates a system that may utilize heterodyne detection to reduce the noise bandwidth of the measurement and the required digitization rate, in accordance with various embodiments.

FIG. 5 illustrates a Fourier domain sensing system 550, in accordance with various embodiments, that employs heterodyne detection and signal processing. The optical system 138-f for illumination projection and signal collection may involve any of the systems disclosed as in FIGS. 1, 2, 3A, 3B, 4, 6, 7, and 8. In one embodiment, the acousto-optic spatial modulator 114-f may be driven with a double-sided chirp signal 139-f having linearly time-varying difference frequency, $\Delta v$, and centered at the Bragg frequency, $v_c$, resulting in rapid sequential measurement of spatial frequencies along a Fourier slice. The detected signal 112-f produced as a result of chirped sequential Fourier sampling may itself be chirped in frequency, varying in time with the difference frequency $\Delta v$. If the detector signal is processed directly, photon shot noise as well as other white noise processes 140-f from the entire detector bandwidth, $v_{BW}$, may corrupt the digitized signal. On the other hand, by electronically mixing and/or multiplying the detector signal 112-f, for example, with a synchronously chirped reference signal 141-f using an analog circuit 142-f, the chirped detector signal may be modulated onto a fixed carrier at the heterodyne offset frequency, $v_h$. By passing the heterodyne signal through a bandpass filter 143-f with a bandwidth of $\Delta v_{BP}$ centered at $v_h$, it may be possible to reduce the noise bandwidth 140-f of the signal to be digitized 144-f by a factor of N, where N is the number of resolvable spatial frequencies in the Fourier slice and may be determined by the time-bandwidth product of the acousto-optic Bragg cell 114-f. Furthermore, by choosing $v_h$ to be low, the digitizer sampling rate may be reduced by up to a factor of N, making it possible to use a lower bandwidth, higher dynamic range digitizer. In some embodiments, the same heterodyne detection effect can be achieved optically instead of electronically by modulating the amplitude of the illumination source 104-f using the chirped reference signal, as illustrated by the dashed line 145-f. In this case, the detector signal 112-f may be passed directly through the bandpass filter 143-f without mixing. Such optical heterodyne detection may reduce the detector bandwidth requirement by up to a factor of N and may avoid nonlinearities associated with electronic mixing and multiplication.

It should be apparent to those skilled in the art that a variety of implementations of the embodiment in FIG. 5 are possible within the spirit and scope of this invention, including such variations as are seen with embodiments of FIG. 1-4. Furthermore, various components of FIG. 5 may be labeled with first reference numbers that may be described above along with FIGS. 1, 2, 3A, 3B, and/or 4. A second reference label on a component may merely reflect that the component is part of a specific figure.

Figure 6:
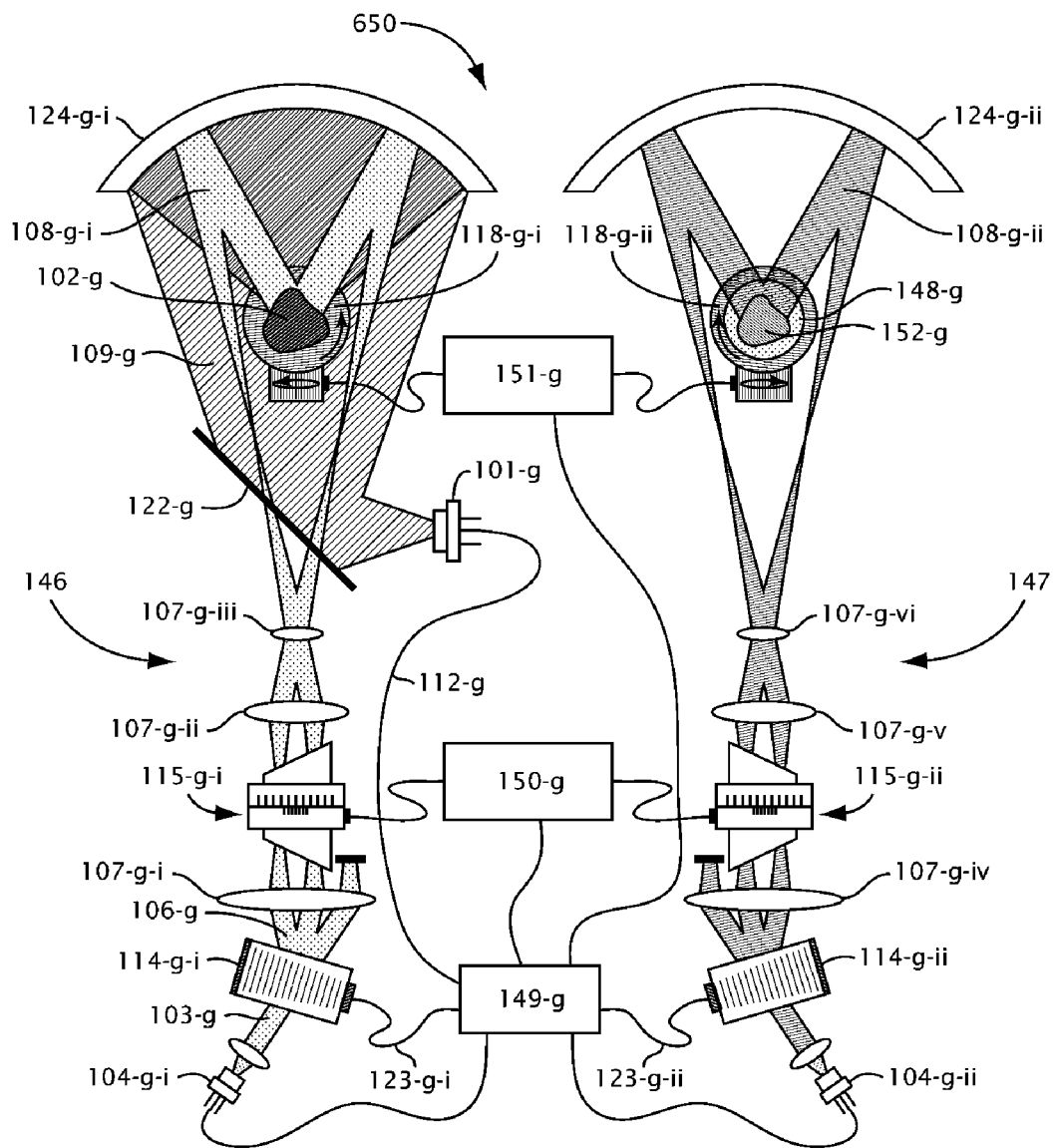
FIG. 6 illustrates a system wherein a Fourier analysis system may be interfaced with a nearly identical Fourier synthesis system for synchronously writing Fourier components of the object into a suitable bias-subtracting recording medium, in accordance with various embodiments.

FIG. 6 illustrates a Fourier domain sensing and writing system 650, in accordance with various embodiments that involves a three-dimensional holographic copier. In some embodiments, the Fourier domain sensing and writing system 650 may include a Fourier domain sensing system 146 such as that illustrated in FIG. 3A (systems 350) for example. Other Fourier domain sensing systems may also be used in some embodiments of system 650. System 146 may be controlled synchronously with an Fourier domain writing system 147. In one embodiment, the writing system 147 may be similar to the sensing system 146, except that no radiation from the object 109-g is detected by system 147. Rather, a suitable recording medium 148-g may be used in place of the object. A controller 149-g may be used to produce the drive signals for the light sources 104-g-i, 104-g-ii and spatial modulators 114-g-i, 114-g-ii in the sensing and writing systems 146 and 147 respectively, to process the detector signal 112-g from the sensing system to compute Fourier components of the object 102-g and to synchronously control the drivers 150-g and 151-g for wavefront rotating devices 115-g-i and 115-g-ii and tilt stages 118-g-i and 118-g-ii of the sensing and writing systems. In this embodiment, one or more Fourier components along a slice in Fourier space may be first measured by the sensing system 146 as described above, either simultaneously using frequency-multiplexed illumination or sequentially using a frequency-stepped drive signal 123-g-i. Additionally, the sensing system radiation source 104-g-i may be modulated in amplitude to step the phase of the structured illumination or to implement heterodyne sensing as described earlier. After the amplitudes and phases of the measured Fourier components along a Fourier slice are computed, the spatial modulator 114-g-ii in the writing system 147 may be programmed with a waveform 123-g-ii synthesized from the up-shifted coherent sum of these measured Fourier components. Once the synthesized pattern fills the spatial modulator 114-g-ii, the writing system light source 104-g-ii may be briefly pulsed, thereby illuminating 108-g-ii the recording medium 148-g with a stationary pattern comprising the measured Fourier components. This process may be repeated as additional Fourier components along the Fourier slice are measured and as the object 102-g and recording medium 148-g are synchronously rotated and/or tilted to copy additional Fourier slices and build up an image 152-g of the object 102-g. Because Fourier components from separate measurements may be combined incoherently in the recording medium, a uniform bias may accumulate as a result of such optical Fourier synthesis. To avoid image saturation, a suitable recording medium that is sensitive to spatial intensity variations, but not uniform bias, such as a photorefractive medium, may be used. For two-dimensional recording, a bias-subtracting CCD detector can instead be used as a recording medium 148-g in which a fixed amount of accumulated charge may be removed from each well several times during the integration period as multiple patterns sequentially illuminate the CCD surface. Alternatively, with precise illumination control, a thresholding recording medium 148-g, such as photoresist, can be used to produce high-contrast recordings of weak accumulated patterns on top of a large uniform bias.

It should be apparent to those skilled in the art that a variety of implementations of the embodiment illustrated in FIG. 6 are possible within the spirit and scope of this invention. The reading and writing processes and the control of rotation and tilt stages may be synchronous or sequential. The projected patterns may be electronically or optically scaled or otherwise altered to synthesize a scaled, filtered, or otherwise modified replica 152-g of the object 102-g. The writing system 147 may be implemented within the same optical system as the reading system 146, so that the object 102-g may be replaced with the recording medium 148-g after the measurement process has completed to initiate the writing process. Alternatively, the object 102-g and recording medium 148-g may be placed side-by-side within the illumination field of the same system. Furthermore, the writing system 147 may be used independently from the sensing system 146 as a Fourier synthesis engine. The optical architectures of the sensing and writing systems may differ from the one shown and may resemble embodiments illustrated in the other figures, such as FIGS. 1, 2, 4, 3B, 5, 7, and 8. The spatial modulators 114-g may be one-dimensional as shown or two-dimensional. When spatial modulator 114-g-ii used in the writing system 147 is a two-dimensional spatial modulator, two-dimensional coherently-synthesized patterns may be written into the recording medium 148-g, which may thereby reduce bias accumulation. Pulsing of the illumination, whether by strobing the light source and/or shuttering the illumination itself, may be used when the spatial modulation pattern is moving as in the case of an acousto-optic device. On the other hand, with parallel-programmable spatial modulators such as LCD or DMD arrays, illumination pulsing may not be necessary.

It should be apparent to those skilled in the art that a variety of implementations of the embodiment in FIG. 6 are possible within the spirit and scope of this invention, including such variations as are seen with embodiments of FIGS. 1-5. Furthermore, various components of FIG. 6 may be labeled with first reference numbers that may be described above along with FIGS. 1, 2, 3A, 3B, 4, and/or 5. A second reference label on a component may merely reflect that the component is part of a specific figure.

Figure 7:
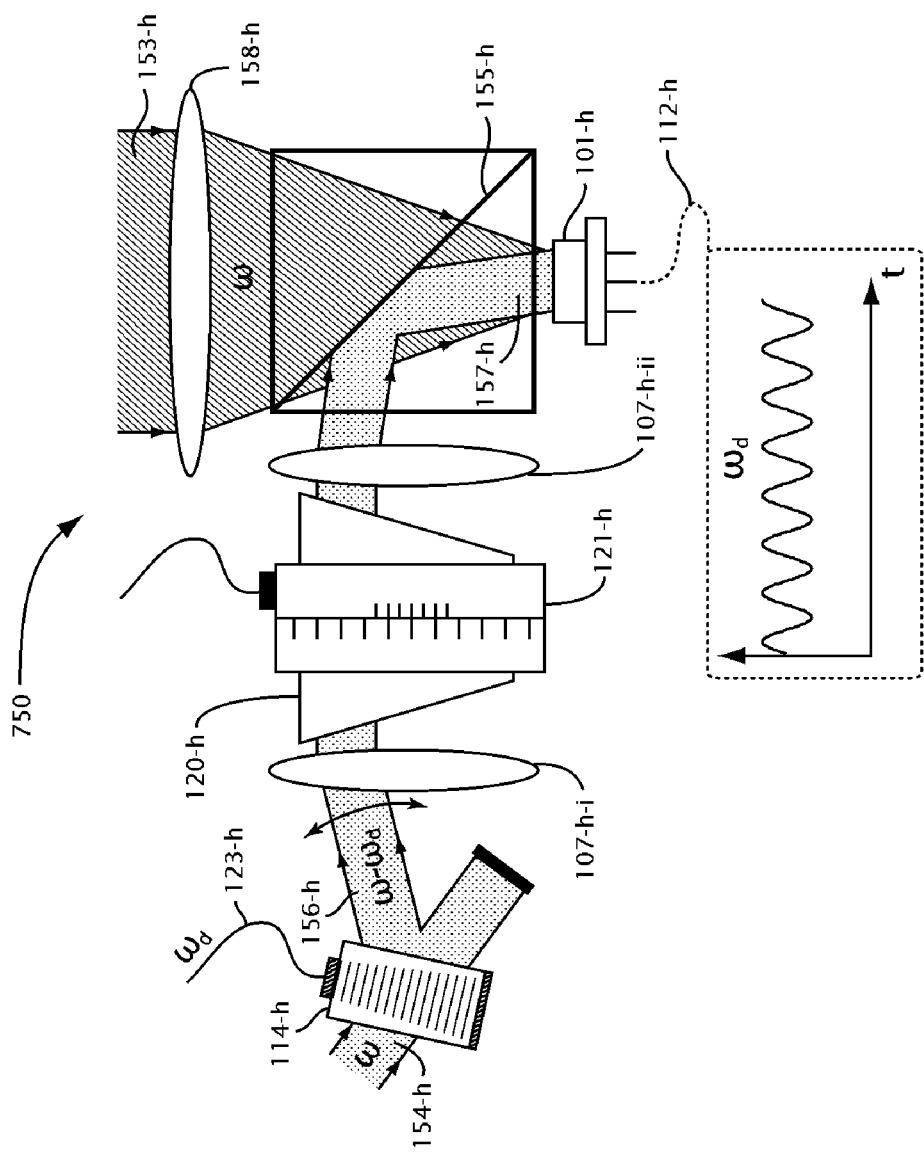
FIG. 7 illustrates a system for passive remote sensing that may measure the complex Fourier components of a coherent wavefront using an acousto-optically frequency-shifted and tilted reference beam, a rotating prism, and a single-element detector, in accordance with various embodiments.

FIG. 7 illustrates a passive remote coherent optical Fourier domain sensing system 750, in accordance with various embodiments. Whereas embodiments illustrated in FIG. 1-FIG. 6 may rely on illuminating the object with patterned radiation, in this embodiment plane wave components of a coherent wavefront 153-h of frequency ω from a remote object (not shown) may be measured passively. In one embodiment, a coherent reference beam 154-h with frequency ω may be diffracted by an acousto-optic spatial modulator 114-h driven with an RF tone 123-h of frequency $\omega_d$, rotated using a prism 120-h, and coherently combined using a beam splitter 155-h with the wavefront 153-h from the object on the surface of a single-element detector 101-h. The frequency of the diffracted beam 156-h may be Doppler-shifted by $\omega_d$ as a result. In this case, the plane wave component of the object wavefront matching the direction of the Doppler-shifted and tilted reference beam 157-h illuminating the detector 101-h results in a beat signal at the detector output 112-h with frequency $\omega_d$, whereas other plane wave components produce interference patterns that are spatially integrated at the detector surface, generating little or no net signal modulation. By varying the tilt of the reference beam 157-h acousto-optically and changing its direction using the rotation stage 121-h, plane wave components of the wavefront 153-h from the object can be sequentially measured and processed in any of the numerous ways described in the context of the various structured illumination embodiments. Furthermore, by driving the Bragg cell 114-h with a compound signal 123-h with multiple frequencies, it may be possible to measure multiple plane wave components of the object wavefront 153-h simultaneously, in a manner as was described in the context of FIG. 1 and FIG. 2, for example. While in structured illumination embodiments such frequency-multiplexed measurements may reduce the depth of field due to tilt ambiguity, in this embodiment no analogous ambiguity or drawback may exist. The object wavefront 153-h may be collected onto the detector 101-h using an optical system such as a lens 158-h such that the phase gradient imparted on the wavefront 153-h by the optical system may be subtracted during processing of the detector signal to reveal the phase distribution of the incident wavefront.

This Fourier-domain wavefront analysis technique has several features that may be compared with other wavefront analysis methods. Because an individual single-element detector 101-$h$ may be used to fully characterize the complex wavefront, this technique can be used in wavelength regimes where detector arrays are expensive or not available. The use of reflective spatial modulator and wavefront rotation technologies and a membrane beam splitter may extend this technique to EUV and X-ray regimes. In holography applications, the single-element detector 101-$h$ can replace high-resolution film and/or high density imaging detectors in measuring the field and amplitude distribution of a coherent wavefront. Since the directions of the reference beam and the measured plane wave component are always co-aligned, this technique can be used to measure the entire complex Fourier transform of the wavefront with uniform accuracy. Furthermore, heterodyne detection and signal processing techniques can be applied to reduce the noise bandwidth as well as detector and digitization bandwidth requirements as described in the context of FIG. 5.

It should be apparent to those skilled in the art that a variety of implementations of the embodiment illustrated in FIG. 7 are possible within the spirit and scope of this invention. The coherent reference beam 154-$h$ may be derived from the radiation used to illuminate the object, created by diverting a portion of the object wavefront 153-$h$, or produced by a frequency-locked laser. In the latter case, state-of-the art locking stability may not be necessary since the acousto-optic Doppler shift is typically in the range of tens to hundreds of megahertz. The wavefront rotation device 121-$h$ may be reflecting, including a retro-reflecting prism and/or an arrangement of mirrors. Measurements along different directions can be accomplished by rotating the reference beam 157-$h$ and/or rotating the object wavefront 153-$h$. As in embodiments described earlier, the spatial modulator 114-$h$ may be a one dimensional device such as an acousto-optic Bragg cell, a SAW device, or a programmable grating device, or a two-dimensional device such as a multi-dimensional acousto-optic Bragg cell, LC device, or DMD array. In some embodiments with a two-dimensional spatial modulator 114-$h$ wavefront rotation may not be necessary. The two dimensional Bragg cell can be a single device, or can comprise two orthogonal one-dimensional Bragg cells. Furthermore, with a two-dimensional Bragg cell, each reference beam tilt and orientation can be encoded with a unique RF frequency, making possible parallel frequency-multiplexed measurement of the two-dimensional complex Fourier transform of the object wavefront 153-$h$ by frequency analysis of the time-domain detector signal.

It should also be apparent to those skilled in the art that a variety of implementations of the embodiment in FIG. 7 are possible within the spirit and scope of this invention, including such variations as are seen with embodiments of FIGS. 1-6. Furthermore, various components of FIG. 7 may be labeled with first reference numbers that may be described above along with FIGS. 1, 2, 3A, 3B, 4, 5, and/or 6. A second reference label on a component may merely reflect that the component is part of a specific figure.

Figure 8:
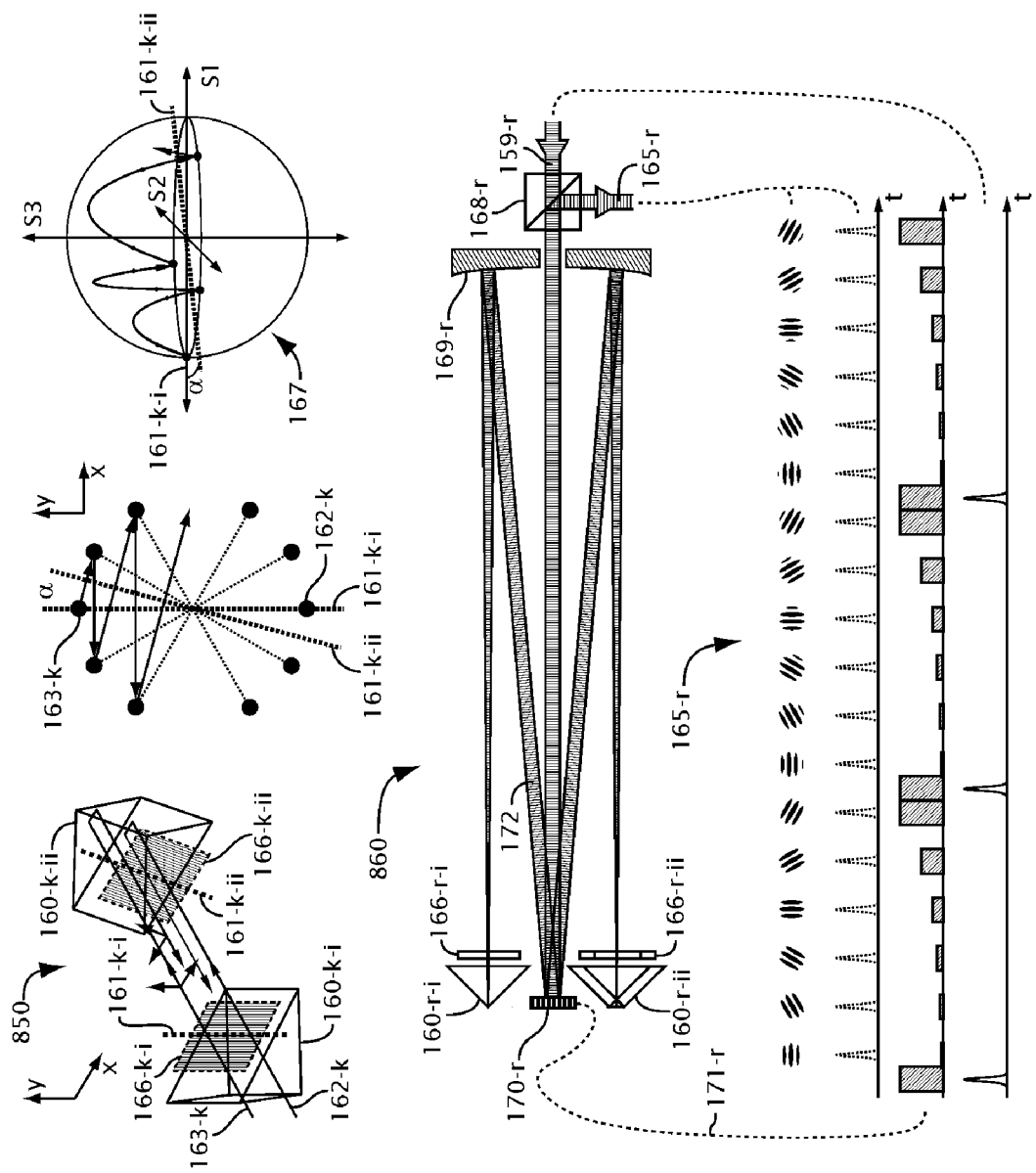
FIG. 8 illustrates a system that may provide a means for rotating a wavefront without moving components using mutually-tilted retro-reflecting prisms or mirrors inside a pulsed laser mirror cavity, in accordance with various embodiments.

FIG. 8 illustrates aspects of a Fourier domain sensing system 850 for rotating a wavefront without moving components employing retro-reflection, in accordance with various embodiments. Non-mechanical wavefront rotation may be accomplished by multiple reflection of a spatially modulated pulsed radiation wavefront by a pair of opposing right-angle retro-reflecting prisms or mirrors 160-$k$-$i$ and 160-$k$-$ii$, collectively referred to as a "retro-reflector cavity", whose reflection symmetry axes 161-$k$-$i$ and 161-$k$-$ii$ are slightly tilted with respect to each other by an angle $\alpha$. This process is illustrated for a pair of co-aligned radiation beams 162-$k$ and 163-$k$. With each pass through the retro-reflector cavity, the transverse pattern defined by the two beams is incrementally rotated by an angle $2\alpha$ and a fraction of the radiation may be coupled out of the cavity, producing a sequence of pulsed radiation patterns having different orientations 165-$r$ (discussed below). In some embodiments, birefringent phase retarders 166-$k$-$i$ and 166-$k$-$ii$ may be placed in front of each retro-reflector, their fast or slow axes aligned with the reflection symmetry axis of the corresponding retro-reflector 160-$k$, in order to rotate the polarization of the pulsed wavefront at the rate of pattern rotation. The thickness of each retarder 166-$k$ may be chosen so that together with the retro-reflector 160-$k$, a half-wave relative phase retardatance may be produced between the eigen-polarizations after each retro-reflection, resulting in an incremental tilt of the linear polarization axis by $2\alpha$ upon each pass through the cavity, as illustrated on the Poincaré sphere 167.

Also illustrated are aspects of wavefront rotating using a pulsed laser mirror cavity system 860, in accordance with various embodiments. In this embodiment, a pulse of structured radiation 159-$r$, which may be produced by a laser, such as a Ti:Sapphire femtosecond laser merely by way of example, may be coupled into the cavity via a beam splitter 168-$r$ through a hole in a curved mirror 169-$r$. A programmable grating 170-$r$, such as a Grating Light Valve (GLV) or a Surface Acoustic Wave (SAW) device, positioned near the center of the focal plane of the curved mirror 169-$r$ may be used to diffract a fraction of the incident radiation 159-$r$ in response to a control signal 171-$r$. The $1^{st}$ order diffracted radiation 172 from the programmable grating may be focused by the curved mirror 169-$r$ onto a retro-reflector 160-$r$ positioned at a location near the center of the focal plane of the curved mirror 169-$r$. Other diffraction orders of the radiation may also be used in some embodiments. A retarder 166-$r$ may be placed in front of the retro-reflector 160-$r$ for polarization rotation as described earlier. The retro-reflected radiation may be directed once again onto the programmable grating 170-$r$. In response to the control signal 171-$r$, the programmable grating may diffract a portion 165-$r$ of the incident radiation back through the hole in the curved mirror to be coupled out of the cavity via the beam splitter 168-$r$. Another portion 172 of the incident radiation may be reflected by the programmable grating 170-$r$ towards the curved mirror 169-$r$, which may focus the radiation reflected from the grating 170-$r$ onto a second retro-reflector 160-$r$ whose reflection symmetry axis is tilted with respect to that of the first retro-reflector 160-$r$. Again, another retarder 166-$r$ may be placed in front of the retro-reflector 160-$r$ for polarization rotation. The retro-reflected radiation may be directed by the curved mirror 169-$r$ onto the programmable grating 170-$r$ and the process described above may be repeated multiple times, producing a sequence of rotated patterns 165-$r$ at the cavity output. As illustrated, the grating control signal 171-$r$ may vary in time such that an equal radiation intensity is coupled out of the cavity system 860 for each rotated pattern and the pulse energy within the cavity system 860 may be substantially depleted upon the full rotation of the pattern, at which point another radiation pulse may be coupled into the cavity system 860 as described above and the process repeats.

It should be apparent to those skilled in the art that a variety of implementations of the embodiment illustrated in FIG. 8 are possible within the spirit and scope of this invention. The retro-reflectors 160-$r$ may be positioned at other locations within a mirror cavity system 860, such as the Fourier plane. The cavity system 660 may be unfolded such that a pair of lenses may be used instead of the curved mirror 169-*r*. In this case, a Bragg cell may be used instead of a programmable grating 170-*r*. The programmable grating 170-*r* or Bragg cell may also be used to spatially modulate the incident radiation 159-*r* to create a desired pattern, in which case the incident radiation may be unstructured. A passive wavefront rotation system can be designed in which the programmable grating 170-*r* may be replaced with a partially-reflecting mirror serving as both, an input and output coupler. In this embodiment, the beam splitter 168-*r* is not used and the incident wavefront 159-*r* enters the cavity through the coupling mirror. Furthermore, a gain medium may be added to the cavity system 860 to enhance its efficiency.

It should also be apparent to those skilled in the art that a variety of implementations of the embodiment in FIG. 8 are possible within the spirit and scope of this invention, including such variations as are seen with embodiments of FIGS. 1-7. Furthermore, various components of FIG. 8 may be labeled with first reference numbers that may be described above along with FIGS. 1, 2, 3A, 3B, 4, 5, 6, and 7. A second reference label on a component may merely reflect that the component is part of a specific figure.

Figure 9:
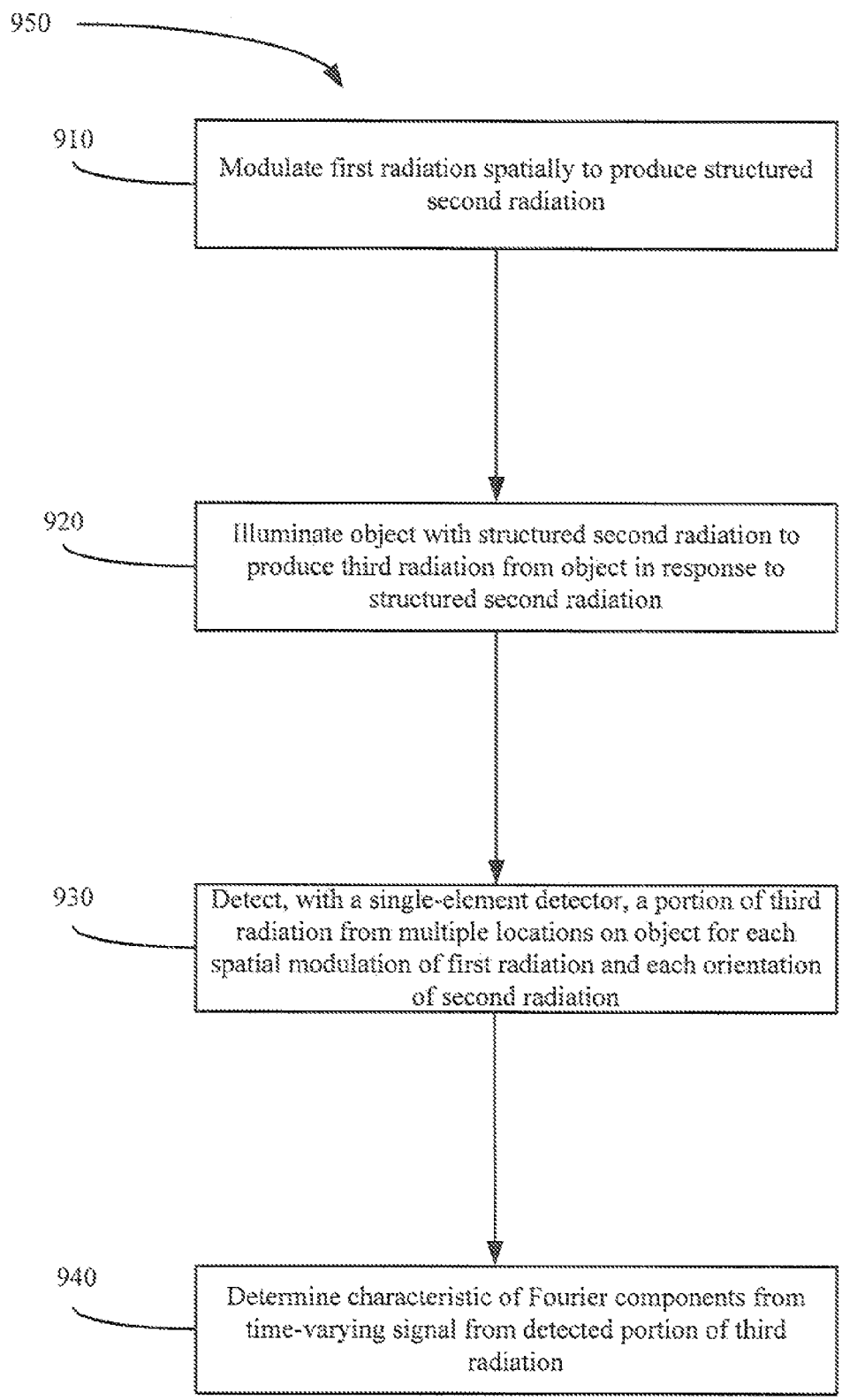
FIG. 9 is a flowchart of a method of measuring one or more sinusoidal Fourier components of an object, in accordance with various embodiments.

FIG. 9 is a flow chart illustrating a method 950 of measuring one or more sinusoidal Fourier components of an object. The method 950 may, for example, be performed in whole or in part within the systems of FIGS. 1-8. Further aspects and additional embodiments of method 950 may be more thoroughly discussed within the description provided within these systems and are thus not necessarily repeated here.

At block 910, a first radiation is spatially modulated resulting in a structured second radiation. Spatially modulating the first radiation utilizes a variety of different modulators including, but not limited to, a one-dimensional acousto-optic Bragg cell, a multi-dimensional acousto-optic Bragg cell, a surface acoustic wave device, a programmable grating device, a liquid crystal array, or a digital micromirror device. In some embodiments, spatially modulating the first radiation may be along multiple non-parallel directions. Spatially modulating the first radiation may depend on the object and/or a structure of the structured second radiation.

The first radiation may be visible and/or invisible, particulate and/or wavelike, and may be temporally and/or spatially coherent, as in the case of laser radiation, and/or partially coherent, as in the case of radiation from a Light Emitting Diode (LED). In some embodiments, the first radiation may have a spectral distribution, such as a broadband radiation. A first radiation with spectral distribution may be partially spatially coherent. The first radiation may be pulsed in some embodiments. The first radiation may be amplitude modulated in time in some embodiments. Spatially modulating the first radiation may also include phase modulation, polarization modulation, and/or amplitude modulation. The spatial modulation may be along a single direction or along multiple directions.

In some embodiments, generating the second structured radiation may be controlled to reduce errors in the structured second radiation. The relative strengths of the sinusoidal Fourier components of the structured second radiation may be varied in some embodiments. In some embodiments, spatial frequencies present in the structured second radiation may be non-redundant.

At block 920, the object is illuminated with the structured second radiation to produce a third radiation from the object in response to the illuminating. The structured second radiation may be scaled and oriented relative to the object. Orienting the second radiation relative to the object may include orienting the structured illumination relative to a reference frame. Orienting the second radiation relative to the object may include orienting the object relative to a reference frame. A reference frame may be defined by a Fourier domain sensing system within which method 950 may be implemented.

At block 930, a single-element detector detects a portion of the third radiation from multiple locations on the object simultaneously for each spatial modulation of the first radiation and for each orientation of the second structured radiation. The third radiation may include radiation that is scattered, reflected, transmitted, fluoresced, and/or otherwise generated by the object.

In some embodiments, multiple single-lement detectors may be used, wherein each of the single-element detectors detects a portion of the third radiation from multiple locations on the object. The detected portion of the third radiation detected by each of the multiple single-element detectors may have a substantially different wavelength and may be due to substantially different Fourier components of the object than radiation detected by one or more other the single-element detectors.

In some embodiments, the phase of one or more sinusoidal Fourier components of the spatial modulation may be changed between multiple successive detection times. The spatial frequency of one or more sinusoidal Fourier components of the spatial modulation may be changed between multiple successive detection times. The orientation of the structured second radiation with respect to the object may be changed between multiple successive detection times. The strength of one or more sinusoidal Fourier components of the structured second radiation may be changed between multiple successive detection times.

At block 940, characteristics of the sinusoidal Fourier components of the object are estimated based on a time-varying signal from the detected portion of the third radiation. The characteristics may include a phase, a weighted sum of the phases, an amplitude, or a weighted sum of the amplitudes of the sinusoidal Fourier components of said object, merely by way of example.

In some embodiments, method 950 may also include reconstructing an image of the object. The image may be reconstructed from the measured sinusoidal Fourier components of the object. The image may be one dimensional, two dimensional, or three dimensional. In some embodiments, reconstructing an image of the object may involve a direct Fourier transformation of the measured Fourier components of the object. In some embodiments, depth of field and resolution of the image may be substantially decoupled. The resolution of the reconstructed image may surpass the diffraction limit of the optical system receiving the radiation from the object. In some embodiments, geometrical parameters of the object, such as position, orientation, and scaling, may also be determined from the measured Fourier components.

In some embodiments, method 950 may also include calculating at least one projection of the objected based on the time-varying signal. From the projections, an image may be reconstructed in some embodiments by applying a tomographic filtered backprojection algorithm to one or more projections.

In some embodiments, method 950 may also include synthesizing a structure or image of the object by illuminating a recording medium with a sequence of radiation patterns. Each radiation pattern may include one or more characterized Fourier components. The recording medium may include a variety of media including, but not limited to, a bias-subtracting detector array, a photorefractive crystal, or a photoresist.

In some embodiments, method 950 may include estimated characteristics of sinusoidal Fourier components of the object that may form a sparse subset of a Fourier basis set of the object. The sparse subset may be chosen to efficiently image a class of objects and/or to better utilize the information throughputs and/or capacities of the optical, electronic, and/or processing systems. In some embodiments, the object may be classified based on characteristics of the sinusoidal Fourier components of the object. In some embodiments, the classification maybe made by using structured illumination that includes Fourier components of a matched filter.

In some embodiments, method 950 may also include modulating the time-varying detected signal onto a carrier signal having a substantially fixed frequency by electronically mixing the time-varying detected signal with a time-varying reference signal. Some embodiments may include modulating the structured second radiation with a time-varying reference signal to produce the time-varying detected signal having a substantially fixed frequency within a bandwidth of the detector. Modulating the structured second radiation may include amplitude, frequency, phase, and/or polarization modulation.

Figure 10:
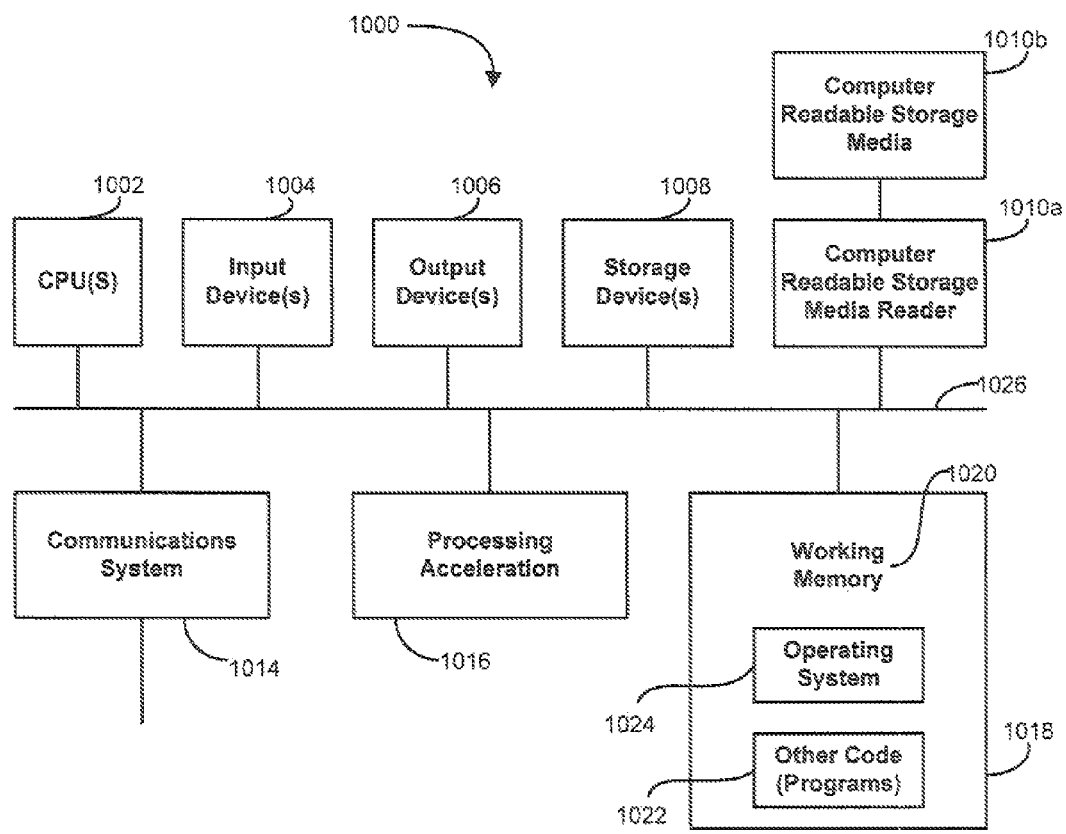
FIG. 10 is a schematic illustration of a computational device that may be used in part to implement embodiments of Fourier domain sensing systems, apparatuses, and methods, in accordance with various embodiments.

The methods, apparatuses, and systems described in connection with method 950 and systems 180, 250, 350, 360, 450, 550, 650, 750, 850, and 860 may be implemented in part by using a computational device 1000 such as shown schematically in FIG. 10, which broadly illustrates how individual system elements may be implemented in a separated or more integrated manner. The device 1000 is shown comprised of hardware elements that may be electrically coupled via bus 1026. The hardware elements may include a processor 1002, an input device 1004, an output device 1006, a storage device 1008, a computer-readable storage media reader 1010a, a communications system 1014, a processing acceleration unit 1016 such as a DSP or special-purpose processor, and a memory 1018. The computer-readable storage media reader 1010a may be further connected to a computer-readable storage medium 1010b, the combination comprehensively representing remote, local, fixed, and/or removable storage devices plus storage media for temporarily and/or more permanently containing computer-readable information. The communications system 1014 may comprises a wired, wireless, modem, and/or other type of interfacing connection and permits data to be collected from the Fourier domain sensing systems. In some instances, such data collection may be performed in real time by the communications system. In some instances, one or more characteristics of the measured Fourier components may be computed from such collected data by using a lookup table stored within the memory 1018, storage device 1008, on computer readable storage media 1010, and/or within storage elements embedded within the processor 1002 and/or processor acceleration unit 1016.

The device 1000 may also include software elements, shown as being currently located within working memory 1020, which may include an operating system 1024 and other code 1022, such as a program designed to implement methods of the invention. Merely by way of example, device 1000 may include processing code that may include instructions to determine one or more characteristics of sinusoidal Fourier components of the object based on a time-varying signal, merely by way of example. Processing code may also be included to reconstruct, synthesize, display, and/or analyze images of the object. Code may also be included to control and/or to implement embodiments of different Fourier domain sensing systems. It will be apparent to those skilled in the art that substantial variations may be used in accordance with specific requirements. For example, customized hardware might also be used and/or particular elements might be implemented in hardware, software (including portable software, such as applets), or both. Further, connection to other computing devices such as network input/output devices may be employed.

It should be noted that the methods, systems, and devices discussed above are intended merely to be examples. It must be stressed that various embodiments may omit, substitute, or add various procedures or components as appropriate. For instance, it should be appreciated that, in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known circuits, processes, algorithms, structures, and techniques have been shown without unnecessary detail in order to avoid obscuring the embodiments.

Also, it is noted that the embodiments may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure.

Moreover, as disclosed herein, the term "memory" or "memory unit" may represent one or more devices for storing data, including read-only memory (ROM), random access memory (RAM), magnetic RAM, core memory, magnetic disk storage mediums, optical storage mediums, flash memory devices, or other computer-readable mediums for storing information. The term "computer-readable medium" includes, but is not limited to, portable or fixed storage devices, optical storage devices, wireless channels, a sim card, other smart cards, and various other mediums capable of storing, containing, or carrying instructions or data.

Furthermore, embodiments may be implemented by hardware, software, firmware, middleware, microcode, hardware description languages, or any combination thereof. When implemented in software, firmware, middleware, or microcode, the program code or code segments to perform the necessary tasks may be stored in a computer-readable medium such as a storage medium. Processors may perform the necessary tasks.

Having described several embodiments, it will be recognized by those of skill in the art that various modifications, alternative constructions, and equivalents may be used without departing from the spirit of the invention. For example, the above elements may merely be a component of a larger system, wherein other rules may take precedence over or otherwise modify the application of the invention. Also, a number of steps may be undertaken before, during, or after the above elements are considered. Accordingly, the above description should not be taken as limiting the scope of the invention, which is defined in the following claims.

What is claimed is:

1. A method for measuring one or more spatial Fourier components of an object, the method comprising:
   generating a structured second radiation by spatially modulating a first radiation;
   illuminating said object with said structured second radiation, the illuminating radiation comprising one or more moving sinusoidal components having at least one of a distinct scaling, orientation, or equation of motion with respect to the object, such that said object produces a third radiation in response to said illuminating;

detecting, with a single-element detector, a portion of said third radiation from a plurality of locations on said object substantially simultaneously; and estimating at least one characteristic of said one or more spatial Fourier components of said object based on a time-varying signal from said detected portion of said third radiation.

2. The method of claim 1 wherein said at least one characteristic comprises at least one of a phase, a weighted sum of the phases, an amplitude, or a weighted sum of the amplitudes of said one or more spatial Fourier components of said object.

3. The method of claim 1 wherein spatially modulating said first radiation utilizes at least one of a one-dimensional acousto-optic Bragg cell, a multi-dimensional acousto-optic Bragg cell, a surface acoustic wave device, a programmable grating device, a liquid crystal array, or a digital micromirror device.

4. The method of claim 1 further comprising reconstructing an image of said object from said at least one characteristic of said one or more spatial Fourier components of said object.

5. The method of claim 4 wherein said image is two-dimensional.

6. The method of claim 4 wherein said image is three dimensional.

7. The method of claim 4 wherein reconstructing said image further comprises a direct Fourier transformation of said one or more spatial Fourier components of said object.

8. The method of claim 4 further comprising calculating one or more projections of the object from said time-varying signal.

9. The method of claim 8 wherein said image is reconstructed by applying a tomographic filtered backprojection algorithm to said one or more projections.

10. The method of claim 1 further comprising synthesizing a structure by illuminating a recording medium with a sequence of radiation patterns based on said measured Fourier components.

11. The method of claim 10 wherein said recording medium comprises at least one of a bias-subtracting detector array, a photorefractive crystal, or a photoresist.

12. The method of claim 1 wherein spatially modulating said first radiation comprises at least one of amplitude modulation, phase modulation, wavelength modulation, or polarization modulation.

13. The method of claim 1 wherein spatially modulating said first radiation is along a plurality of non-parallel directions.

14. The method of claim 1 wherein said first radiation has a spectral distribution.

15. The method of claim 14 wherein said first radiation having a spectral distribution is partially spatially coherent.

16. The method of claim 1 further comprising a plurality of single-element detectors, wherein each of said plurality of single-element detectors detects a portion of said third radiation from a plurality of locations on said object.

17. The method of claim 16 wherein said portion of said third radiation detected by each of said plurality of single-element detectors has a substantially different wavelength and is due to substantially different Fourier components of said object than radiation detected by one or more other said single-element detectors.

18. The method of claim 1 wherein the illuminating radiation is oriented relative to said object and said orienting comprises at least one of orienting said structured second radiation relative to a reference frame or orienting said object relative to the reference frame.

19. The method of claim 1 further comprising modulating said time-varying detected signal onto a carrier signal having a substantially fixed frequency by electronically mixing said time-varying detected signal with a time-varying reference signal.

20. The method of claim 1 further comprising modulating said structured second radiation with a time-varying reference signal to produce the time-varying detected signal having a substantially fixed frequency within a bandwidth of said detector.

21. The method of claim 1 wherein said first radiation is at least one of pulsed or amplitude modulated in time.

22. The method of claim 1 wherein said third radiation is at least one of scattered, reflected, transmitted, fluoresced, or otherwise generated by said object.

23. The method of claim 1 wherein spatially modulating said first radiation depends on at least one of said object or a structure of said structured second radiation.

24. The method of claim 1 further comprising controlling said generating of said structured second radiation to reduce errors in a wavefront of said structured second radiation.

25. The method of claim 4 wherein a depth of field and a resolution of said image are substantially decoupled.

26. The method of claim 4 wherein said at least one characteristic of said one or more spatial Fourier components form a sparse subset of a Fourier basis set of said object, wherein said sparse subset is chosen to efficiently image a class of objects.

27. The method of claim 1 further comprising classifying the object based on said at least one characteristic of said one or more spatial Fourier components.

28. A system for measuring one or more spatial Fourier components of an object, the system comprising:

a spatial modulator to spatially modulate a first radiation to produce a structured second radiation;

a projector to illuminate the object with the structured second radiation, the illuminating radiation comprising one or more moving sinusoidal components having at least one of a distinct scaling, orientation, or equation of motion with respect to the object;

a single-element detector positioned to receive a third radiation from a plurality of locations on the object substantially simultaneously in response to said illuminating, the detector producing a time-varying signal; and a computational unit in communication with said detector, the computational unit having instructions to determine at least one characteristic of said one or more spatial Fourier components of the object from said time-varying signal.

29. A system for measuring one or more spatial Fourier components of an object, the system comprising:

means for producing a structured second radiation by spatially modulating a first radiation;

means for illuminating the object with said structured second radiation, the illuminating radiation comprising one or more moving sinusoidal components having at least one of a distinct scaling, orientation, or equation of motion with respect to the object;

means for detecting a third radiation received from a plurality of locations on the object substantially simultaneously in response to said illuminating; and means for processing a time-varying signal from said detected third radiation to determine at least one characteristic of said one or more spatial Fourier components of said object.

* * * * *